US005955589A

United States Patent [19]
Cook et al.

[11] Patent Number: 5,955,589
[45] Date of Patent: *Sep. 21, 1999

[54] GAPPED 2' MODIFIED OLIGONUCLEOTIDES

[75] Inventors: Phillip Dan Cook, Vista; Brett P. Monia, Carlsbad, both of Calif.

[73] Assignee: Isis Pharmaceuticals Inc., Carlsbad, Calif.

[ * ] Notice: This patent is subject to a terminal disclaimer.

[21] Appl. No.: 08/465,880

[22] Filed: Jun. 6, 1995

Related U.S. Application Data

[63] Continuation-in-part of application No. 08/244,993, filed as application No. PCT/US92/11339, Dec. 23, 1992, Pat. No. 5,623,065, which is a continuation-in-part of application No. 07/814,961, Dec. 24, 1991, abandoned.

[51] Int. Cl.$^6$ ..................... C07H 21/04
[52] U.S. Cl. ............ 536/23.1; 536/25.3; 536/25.2; 536/24.32; 536/24.31; 536/24.3; 536/24.2; 536/24.1; 435/91.1; 435/91.3; 435/91.41; 935/3; 935/6; 935/8
[58] Field of Search .................. 536/25.32, 25.3, 536/25.2, 24.32, 24.31, 24.3, 24.2, 24.1, 23.1; 435/91.1, 91.3, 91.41; 935/3, 6, 8

[56] References Cited

U.S. PATENT DOCUMENTS

| | | | |
|---|---|---|---|
| 4,511,713 | 4/1985 | Miller et al. | 435/6 |
| 4,908,307 | 3/1990 | Rodland et al. | 435/6 |
| 5,013,830 | 5/1991 | Ohtsuka et al. | 536/25.1 |
| 5,034,506 | 7/1991 | Summerton et al. | 528/391 |
| 5,134,066 | 7/1992 | Rogers et al. | 435/91.3 |
| 5,149,797 | 9/1992 | Pederson et al. | 536/23.1 |
| 5,256,775 | 10/1993 | Froehler | 536/25.6 |
| 5,466,786 | 11/1995 | Buhr et al. | 536/26.26 |
| 5,658,731 | 8/1997 | Sproat et al. | 435/6 |

FOREIGN PATENT DOCUMENTS

| | | |
|---|---|---|
| 2017369 | 11/1990 | Canada . |
| 0260032 | 8/1987 | European Pat. Off. . |
| 0 269 574 A2 | 6/1988 | European Pat. Off. . |
| 0339842 | 4/1989 | European Pat. Off. . |
| 0 339 330 | 11/1990 | European Pat. Off. . |
| 39 15 462 | 9/1990 | Germany . |
| 41 10 085 | 10/1992 | Germany . |
| 3-240795 | of 1991 | Japan . |
| WO 90/15814 | 6/1990 | WIPO . |
| WO 91/06556 | 10/1990 | WIPO . |
| WO 91/15499 | 4/1991 | WIPO . |
| WO 91/12323 | 8/1991 | WIPO . |
| WO 94/02498 | 2/1994 | WIPO . |
| WO 92/07065 | 9/1994 | WIPO . |

OTHER PUBLICATIONS

Kawasaki et al. 1991 (Jan.) "Synthesis And Biophysical Studies of 2'–dRIBO–2'–F Modified Oligonucleotides", Conference on Nucleic Acid Therapeutics, Clearwater, FL.
Ikehara et al. 1977 Nucleic Acids Research 4(12): 4249–4260.
Grant et al. (eds.) 1969 in: "Hackh's Chemical Dictionary", McGraw–Hill Book Company, New York, NY, pp. 312 and 274.
Agrawal et al. 1987 Tetrahedron Letters 28(31):3539–3542.
Divakar et al., J. Chem. Soc. Perkin Trans. 1982, 1625.
Khurshid et al., FEBS Letters 1972, 28:1,25.
Kielanowska et al., Nucleic Acids Research 1976, 3:3,817.
Kusmierek et al., ACTA Biochimica Polonica 1973, 20:4, 365.
Pike et al., J. Org. Chem. 1974, 39:25,3674.
Ransford et al., J. Carbohydrates—Nucleosides—Nucleotides 1974, 1:3,275.
Rottman et al., Biochemistry 1974, 13,2762.
Singer et al., Biochemistry 1976, 15:23,5052.
Tazawa et al., Biochemistry 1972, 11, 4931.
Agrawal, S. et al., "Oligodeoxynucleoside Phosphoramidates and Phosphorothioates as Inhibitors of Human Immunodeficiency Virus" Proc. Natl. Acad. Sci. USA 1988 85, 7079–7083.
Augustyns, et. al., "Influence of the Incorporation of (S)–9–(3,4–dihydroxy–butyl)Adenine on the Enzymatic Stability and Base–Pairing Properties of Oligodeoxynucleotides" Nucleic Acids Research 1991, 19, 2587–2593.
Beaton, et. al., Chapter 5, Synthesis of oligonucleotide phosphorodithioates, p. 109, Oligonucleotides and Analogs, A Practical Approach, Eckstein, F., Ed.; The Practical Approach Series, IRL Press, New York, 1991, pp. 109–135.
Borthwick, et al., "Synthesis of Chiral Carbocylic Nucleosides" Tetrahedron 1992, 48, 571–623.
Brill et al., "Synthesis of Deoxydinucleoside Phosphorodithioates", J. Am. Chem. Soc. 1991 113, 3972–3980.
Cohen in Oligonucleotides: Antisense Inhibitors of Gene Expression, CRC Press, Inc., Boca Raton, Fl (1989), pp. 1–255.
Dagle et al., "Physical properties of oligonucleotides containing phosphoramidate–modified internucleoside linkages", Nucleic Acids Research 1991, 19, 1805–1810.
Dagle et al., "Targeted degradation of mRNA in Xenopus oocytes and embryos directed by modified oligonucleotides: studies on An2 and cyclin in embryogenesis", Nucleic Acids Research 1990 18, 4751–4757.
Dagle et al., "Pathways of Degradation and Mechanism of Action of Antisense Oligonucleotides in Xenopus laevis Embryos", Antisense Research and Development 1991 1, 11–20.

(List continued on next page.)

Primary Examiner—Christopher S. F. Low
Attorney, Agent, or Firm—Woodcock Washburn Kurtz Mackiewicz & Norris LLP

[57] ABSTRACT

Oligonucleotides and other macromolecules are provided which have increased nuclease resistance, substituent groups for increasing binding affinity to complementary strand, and subsequences of 2'-deoxy-erythro-pentofuranosyl nucleotides that activate RNase H. Such oligonucleotides and macromolecules are useful for diagnostics and other research purposes, for modulating the expression of a protein in organisms, and for the diagnosis, detection and treatment of other conditions susceptible to oligonucleotide therapeutics.

15 Claims, 9 Drawing Sheets

OTHER PUBLICATIONS

Debart et al., "Intermolecular Radical C–C Bond Formation: Synthesis of a Novel Dinucleoside Linker for Non–anionic Antisense Oligonucleosides", *Tetra.Ltrs.* 1992 33, 2645–2648.

Eder, P.S. and Walder, J.A., "Ribonuclease H from K562 Human Erythroleukemia Cells", *The Journal of Biological Chemistry* 1991 266(10), 6472–6479.

Gagnor, et. al., "α–DNA VI: Comparative Study of α– and β– Anomeric Oligodeoxyribonucleotides in Hybridization to mRNA and in Cell Free Translation Inhibition" *Nucleic Acids Research* 1987, 15, 10419–10436.

Gait, et al., "Synthetic Analogues of Polynucleotides. Part XII. Synthesis of Thymidine Derivatives Containing an Oxyacetamido– or and Oxyformamido–Linkage Instead of a Phosphodiester Group", *J.C.S Perkins I* 1974 1684–1686.

Greenberg, M.E. in Current Protocols in Molecular Biology, (Ausubel, et al., eds.), John Wiley and Sons, NY.

Kawasaki et al., *Synthesis and Biophysical Studies of 2'–dRIBO–2'–F Modified Oligonucleotides,* Conference On Nucleic Acid Therapeutics, Clearwater, FL, Jan. 13, 1991.

Kawasaki et al., "Uniformly Modified 2'–Deoxy–2'–fluoro Phosphorothioate Oligonucleotides as Nuclease–Resistant Antisense Compounds with High Affinity and Specificity for RNA Targets", *J. Med. Chem.* 1993 36, 831–841.

Kierzek, et. al., "Association of 2'–5' Oligoribonucleotides" *Nucleic Acids Research* 1992, 20, 1685–1690.

Kirshenbaur, et. al., *The 5th San Diego Conference: Nucleic Acids: New Frontiers,* Poster abstract 28, Nov. 14–16, 1990.

Matteucci et al., "Deoxyoligonucleotides Bearing Neutral Analogues of Phosphodiester Linkages Recognize Duplex DNA via Triple–Helix Formation" *J. Am. Chem. Soc.* 1991 113, 7767–7768.

Matteucci, Mark "Hybridization Properties of a Deoxyoligonucleotide Containing Four Formacetal Linkages" *Nucleosides & Nucleotides* 1991, 10, 231–234.

Matteucci, "Deoxyoligonucleotide Analogs Based on Formacetal Linkages", *Tetrahedron Letters* 1990 31 2385–2388.

Mertes and Coats, "Synthesis of Carbonate Analogs of Dinucleosides. 3'–Thymidinyl 5'–Thymidinyl Carbonate, 3'–Thymidinyl 5'(5–Fluoro–2'–deoxyuridinyl) Carbonate, and 3'–(5–Fluoro–2'–deoxyuridinyl) 5'–Thymidinyl Carbonate", *J. Med. Chem.* (1969) 12:154–157.

Miller, P.S. et al., "Effects of a Trinucleotide Ethyl Phosphotriester, G'''p(Et)G'''p(Et)U, on Mammalian Cells in Culture" *Biochemistry* (1977) 16, 1988–1996.

Miller et. al., Chapter 6, Synthesis of oligo–2'–deoxyribonucleoside methylphosphonates, p. 137, *Oligonucleotides and Analogs, A Practical Approach,* Eckstein, F., Ed.; The Practical Approach Series, IRL Press, New York, 1991.

Miller and Ts'O "A New Approach to Chemotherapy Based on Molecular Biology and Nucleic Acid Chemistry: Matagen (Masking Tape for Gene Expression)" *Anti–Cancer Drug Design* 1987 2, 117–128.

Miller et al., Ch. 30: Oligonucleotide Inhibitors of Gene Expression in Living Cells: New Opportunities in Drug Design *Annual Reports in Medicinal Chemistry* 1988 295–304.

Monia et al., "Evaluation of 2'–Modified Oligonucleotides Containing 2'–Deoxy Gaps as Antisense Inhibitors of Gene Expression" *J. Bio. Chem.* 1993 208, 14514–14522.

Musicki and Widlanski, Synthesis of Nucleoside Sulfonates and Sulfones *Tetrahedron Letters* 1991, 32, 1267–1270.

Musicki and Widlanski, "Synthesis of Carbohydrate Sulfonates and Sulfonate Esters" *J. of Organic Chemistry* 1990, 55, 4231–4233.

Cormier and Ogilvie, "Synthesis of Hexanucleotide Analogues Containing Diisopropylsilyl Internucleotide Linkages" *Nucleic Acids Res.* 1988, 16, 4583–4594.

Ogilvie and Cormier, "Synthesis of a Thymidine Dinucleotide Analogue Containing an Internucleotide Silyl Linkage" *Tet. Letts.* 1985 26 4159–4162.

Perbost, et al., "Sugar Modified Oligonucleotides I. Carbo–Oligodeoxynucleotides as Potential Antisense Agents" *Biochemical and Biophysical Research Communications* 1989, 165, 742–747.

Petersen et al., "Chemical Synthesis of Dimer Ribonucleotides Containing Internucleotidic Phosphoradithioate Linkages" Tet. Letts. 1990 31, 911–914.

Sagi, et al., "Biochemical Properties of Oligo[(+)–Carbocyclic–Thymidylates] and Their Complexes" *Nucleic Acids Research* 1990, 18, 2133–2140.

Saison–Behmoaras, T., et al., "Short Modified Antisense Oligonucleotides Directed against Ha–ras Point Mutation Induce Selective Cleavage of the mRNA and Inhibit T24 Cells Proliferation" *EMBO J.* 1991 10 1111–1118.

Schneider, et al., "Oligonucleotides Containing Flexible Nucleoside Analogues" *J. Am. Chem. Soc.* 1990, 112, 453–455.

Schenider, K. Christian and Benner, Steven A., "Building Blocks for Oligonucleotide Analogs with Dimethylene––Sulfide, Sulfoxide, and Sulfone Groups Replacing Phosphodiester Linkages" *Tet. Letters* 1990 31 335–338.

Secrist, et. al., "Synthesis and Biological Activity of 4'–Thionucleosides" *Tenth International Roundtable: Nucleosides, Nucleotides and Their Biological Evaluation,* Sep. 16–20, 1992, Abstracts of Papers, Abstract 21.

Stawinski Jacek and Thelin Mats, *Tenth International Roundtable: Nucleosides, Nucleotides and Their Biological Evaluation,* Sep. 78, 1992, Abstracts of Papers, Abstract 80.

Szemzo, et. al., "First Synthesis of Carbocyclic Oligothymidylates" *Tetrahedron Letters* 1990, 31, 1463–1466.

Vasseur, J.–J. et al., "Oligonucleosides: Synthesis of Novel Methylhydroxylamine–Linked Nucleoside Dimer and Its Incorporation into Antisense Sequences", *J. Am. Chem Soc* 1992 114, 4006–4007.

Veeneman, G.H. et al., "Synthesis of Oligodeoxynucleotides Containing Thymidines Linked Via an Internucleosidic–(3'–5')–Methylene Bond", *Recueil des Travaux Chimiques des Pays–Bas* 1990, 109, 7–8 449–451.

Berkowitz, Phillip T. et al., Synthesis of 1,2–Dihydro–1–(2deoxy–β–D–Erythro–pentafuranosyl)–2–Oxopyrazine 4–oxide *J. Med. Chem.* 1973 16:183–184.

Inoue et al., "Sequence–dependent Hydrolysis of RNA Using Modified Oligonucleotide Splints and R Nase H" *Febs. Ltrs.* 1987 215 327–330.

Inoue et al., "Synthesis and Hybridization Studies on Two Complementary Nona(2'–O–Methyl)Ribonucleotides" *Nuc. Acids. Res.* 1987 15, 6131–6148.

Inoue et al., "Synthesis and Properties of Novel Nucleic Acid Probes" *Nuc. Acids Res, Symposium Series* 1985 16, 165–168.

Agris et al., "Inhibition of Vesicular Stomatitis Virus Protein Synthesis and Infection by Sequence–Specific Oligodeoxyribonucleoside Methylphosphonates", *Biochemistry* 1986 25(20), 6268–6275.

Atkinson and Smith, "Solid–Phase Synthesis of Oligodeoxyribonucleotides by the Phosphite–triester Method", *Oligonucleotide Synthesis a practical approach,* Chapter 3, pp. 35–81 (1991).

Biggadike et al., "Short Convergent Route to Homochiral Carbocyclic 2'–Deoxynucleosides and Carbocyclic Ribonucleosides", *J. Chem Soc., Chem Commun.,* 1987 1083–1084.

Brill et al., "Synthesis of Oligodeoxynucleoside Phosphorodithioates via Thioamidites", *J. Am. Chem. Soc.* 1989 111, 2321–2322.

Castle and Seese, "Imidazo[4,5–d]pyridazines I. Synthesis of 4,7–Disubstituted Derivatives", *J. Org. Chem.* 1958 23, 1534–1538.

Cazenave et al., "Enzymatic Amplification of Translation Inhibition of Rabbit β–globin mRNA Mediated by Anti–Messenger Oligodeoxynucleotides Covalently Linked to Intercalating Agents", *Nucleic Acids Research,* 1987 15(12):4717–4736.

Constant et al., "Heterodimeric Molecules Including Nucleic Acid Bases and 9–Aminoacridine. Spectroscopic Studies, Conformations, and Interactions with DNA", *Biochemistry* 1988 27, 3997–4003.

Dreyer and Dervan, "Sequence–Specific Cleavage of Single–Stranded DNA: Oligodeoxynucleotide–EDTA–Fe(II)", *Proc. Natl. Acad. Sci. USA* 1985 82, 968–972.

Freskos, J.N., "Synthesis of 2'–Deoxypyrimidine Nucleosides Via Copper (I) Iodide Catalysis", *Nucleosides & Nucleotides* 1989 8(5&6), 1075–1076.

Jarvi et al., "Synthesis and Biological Evaluation of Dideoxunucleosides Containing a Difluoromethylene Unit", *Nucleosides & Nucleotides* 1989 8(5&6), 1111–1114.

Jayaraman et al., "Selective Inhibition of *Escherichia Coli* Protein Synthesis and Growth by Nonionic Oliogonucleotides Complementary to the 3' End of 16S rRNA", *Proc. Natl. Acad. Sci. USA* 1981 78(3), 1537–1541.

Jones, R.A., "Preparation of Protected Deoxyribonucleosides", from *Oligonucleotide Synthesis–A Practical Approach,* 1991 Chapter 2, pp. 23–34.

Jones et al., "4–Substituted Nucleosides. 5. Hydroxymethylation of Nucleoside 5'–Aldehydes", *J. Org. Chem.* 1979 44(8), 1309–1317.

Kazimierczuk et al., "Synthesis of 2'–Deoxytubercidin, 2'–Deoxyadenosine, and Related 2'–Deoxynucleosides via A Novel Direct Stereospecific Sodium Salt Glycosylation Procedure", *J. Am. Chem. Soc.* 1984 106, 6379–6382.

Le Doan et al., "Sequence–Targeted Chemical Modifications of Nucleic Acids by Complimentary Oligonucleotides Covalently Linked to Porphyrines", *Nucleic Acids Research* 1987 15(21), 8643–8659.

Letsinger et al., "Effects of Pendant Groups at Phosphorus on Binding Properties of d–ApA Analogues", *Nucleic Acids Research* 1986 14(8), 3487–3499.

Matsukura et al., "Phosphorothioate Analogs of Oligodeoxynucleotides: Inhibitors of Replication and Cytopathic Effects of Human Immunodeficiency Virus", *Proc. Natl. Acad. Sci. USA* 1987, 84, 7706–7710.

Meyer et al., "Efficient, Specific Cross–Linking and Cleavage of DNA by Stable, Synthetic Complementary Oligodeoxynucleotides", *J. Am. Chem. Soc.* 1989 111, 8517–8518.

Miller et al., "Biochemical and Biological of Nonionic Nucleic Acid Methylphosphonates", *Biochemistry* 1981 20 1874–1880.

Miller et al., "Nonionic Nucleic Acid Analogues. Synthesis and Characterization of Dideoxyribonucleoside Methylphosphonates", *Biochemistry* 1979 18:5134–5142.

Miller et al., "Synthesis and Properties of Adenine and Thymine Nucleoside Alkyl Phosphotriesters, the Neutral Analogs of Dinucleoside Monophosphates" *J. of Am. Chem. Soc.* 1971 93(24) 6657–6664.

Outten, R.A., "Synthetic 1–Methoxybenzo[d]naptho[1,2–b] pyran–6–one C–Glycosides", *J. Org. Chem.* 1987 52(22), 5064–5066.

Revankar et al., "Synthesis and Antiviral/Antitumor Activities of Certain 3–Deazaguanine Nucleosides and Nucleotides", *J. Med. Chem.* 1984 27, 1389–1396.

Robins et al., "Nucleic Acid Related Compounds. 42. A General Procedure for the Efficient Deoxygenation of Secondary Alcohols. Regiospecific and Stereoselective Conversion of Ribonucleosides to 2'Deoxynucleosides", *J. Am. Chem. Soc.* 1983 105, 4059–4065.

Roelen et al., "Synthesis of Nucleic Acid Methylphosphonthioates", *Nucleic Acids Research* 1988 16(15) 7633–7645.

Ruby and Abelson, "An Early Hierarchic Role of U1 Small Nuclear Ribonucleoprotein in Spliceosome Assembly", *Science* 1988 242 1028–1035.

Sigman, D.S., "Nuclease Acitivity of 1,10–Phenanthroline–Copper Ion", *Acc. Chem. Res.* 1986 19, 180–186.

Smith et al., "Antiviral Effect of an Oligo(nucleoside Methylphosphonate) Complementary to the Splice Junction of Herpes Simplex Virus Type 1 Immediate Early pre–mRNAs 4 and 5", *Proc. Natl. Acad. Sci. USA* 1986 83, 2787–2791.

Stein, C.A., "Physiochemical Properties of Phosphorothioate Oligodeoxynucleotides", *Nucleic Acids Research* 1988 16(8), 3209–3221.

Suciu and Lerner, "Synthesis of 9–(2, 5–dideoxy–β–D–glycero–pent–4–enofuranosyl)adenine", *Carbohydrate Research* 1975 44, 112–115.

Tidd et al., "Evaluation of N–ras Oncogene Anti–Sense, Sense and Nonsense Sequence Methylphosphonate Oligonucleotide Analogues", *Anti–Cancer Drug Design* 1988 3 117–127.

van der Krol, "Modulation of Eukaryotic Gene Expression by Complementary RNA or DNA Sequences", *BioTechniques* 1988 6(10) 958–974.

Walder and Walder, "Role of RNase H in Hybrid–Arrested Translation by Antisense Oligonucleotides", *Proc. Natl. Acad. Sci. USA* 1988 85, 5011–5015.

Yeung et al., "Photoreactivities and Thermal Properties of Psoralen Cross–Links", *Biochemistry* 1988 27 3204–3210.

Zon, G., "Synthesis of Backbone–Modified DNA Analogues for Biological Applications", *Journal of Protein Chemistry* 1987 6(2) 131–145.

GAPPED 2' MODIFIED OLIGONUCLEOTIDES

CROSS-REFERENCE TO RELATED APPLICATIONS

This application is a continuation-in-part of U.S. patent application Ser. No. 08/244,993, filed Jun. 21, 1994 (now U.S. Pat. No. 5,623,065), which is the U.S. national phase application of international application PCT/US92/11339, filed Dec. 23, 1992 (now abandoned), which is a continuation-in-part of U.S. patent application Ser. No. 07/814,961, filed Dec. 24, 1991 (now abandoned), the disclosures of which are herein incorporated by reference.

FIELD OF THE INVENTION

This invention is directed to the synthesis and use of oligonucleotides and macromolecules to elicit RNase H for strand cleavage in an opposing strand. Included in the invention are oligonucleotides wherein at least some of the nucleotides of the oligonucleotides are functionalized to be nuclease resistant, at least some of the nucleotides of the oligonucleotide include a substituent that potentiates hybridization of the oligonucleotide to a complementary strand of nucleic acid, and at least some of the nucleotides of the oligonucleotide include 2'-deoxy-erythro-pentofuranosyl sugar moieties. The oligonucleotides and macromolecules are useful for therapeutics, diagnostics and as research reagents.

BACKGROUND OF THE INVENTION

Oligonucleotides are known to hybridize to single-stranded RNA or single-stranded DNA. Hybridization is the sequence specific base pair hydrogen bonding of bases of the oligonucleotides to bases of target RNA or DNA. Such base pairs are said to be complementary to one another.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$) a characteristic physical property of double helices, denotes the temperature in degrees centigrade, at which 50% helical (hybridized) versus coil (unhybridized) forms are present. $T_m$ is measured by using the UV spectrum to determine the formation and breakdown (melting) of the hybridization complex. Base stacking which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides can be used to effect enzymatic cleavage of a target RNA by using the intracellular enzyme, RNase H. The mechanism of such RNase H cleavage requires that a 2'-deoxyribofuranosyl oligonucleotide hybridize to a target RNA. The resulting DNA-RNA duplex activates the RNase H enzyme and the activated enzyme cleaves the RNA strand. Cleavage of the RNA strand destroys the normal function of the RNA. Phosphorothioate oligonucleotides operate via this type of mechanism. However, for a DNA oligonucleotide to be useful for cellular activation of RNase H, the oligonucleotide must be reasonably stable to nucleases in order to survive in a cell for a time period sufficient for RNase H activation. For non-cellular uses, such as use of oligonucleotides as research reagents, such nuclease stability may not be necessary.

Several publications of Walder et al. describe the interaction of RNase H and oligonucleotides. Of particular interest are: (1) Dagle et al., *Nucleic Acids Research* 1990, 18, 4751; (2) Dagle et al., *Antisense Research And Development* 1991, 1, 11; (3) Eder et al., *J. Biol. Chem.* 1991, 266, 6472; and (4) Dagle et al., *Nucleic Acids Research* 1991, 19, 1805. According to these publications, DNA oligonucleotides having both unmodified phosphodiester internucleoside linkages and modified phosphorothioate internucleoside linkages are substrates for cellular RNase H. Since they are substrates, they activate the cleavage of target RNA by RNase H. However, the authors further note that in Xenopus embryos, both phosphodiester linkages and phosphorothioate linkages are also subject to exonuclease degradation. Such nuclease degradation is detrimental since it rapidly depletes the oligonucleotide available for RNase H activation.

As described in references (1), (2) and (4), to stabilize oligonucleotides against nuclease degradation while still providing for RNase H activation, 2'-deoxy oligonucleotides having a short section of phosphodiester linked nucleotides positioned between sections of phosphoramidate, alkyl phosphonate or phosphotriester linkages were constructed. While the phosphoamidate-containing oligonucleotides were stabilized against exonucleases, in reference (4) the authors noted that each phosphoramidate linkage resulted in a loss of 1.6° C. in the measured $T_m$ value of the phosphoramidate containing oligonucleotides. Such a decrease in the $T_m$ value is indicative of an decrease in hybridization between the oligonucleotide and its target strand.

Other authors have commented on the effect such a loss of hybridization between an oligonucleotide and its target strand can have. Saison-Behmoaras et al., *EMBO Journal* 1991, 10, 1111, observed that even though an oligonucleotide could be a substrate for RNase H, cleavage efficiency by RNase H was low because of weak hybridization to the mRNA. The authors also noted that the inclusion of an acridine substitution at the 3' end of the oligonucleotide protected the oligonucleotide from exonucleases.

U.S. Pat. No. 5,013,830, issued May 7, 1991, discloses mixed oligomers comprising an RNA oligomer, or a derivative thereof, conjugated to a DNA oligomer via a phosphodiester linkage. The RNA oligomers also bear 2'-O-alkyl substituents. However, being phosphodiesters, the oligomers are susceptible to nuclease cleavage.

European Patent application 339,842, filed Apr. 13, 1989, discloses 2'-O-substituted phosphorothioate oligonucleotides, including 2'-O-methylribooligonucleotide phosphorothioate derivatives. The above-mentioned application also discloses 2'-O-methyl phosphodiester oligonucleotides which lack nuclease resistance.

U.S. Pat. No. 5,149,797, issued Sep. 22, 1992, discloses mixed phosphate backbone oligonucleotides which include an internal portion of deoxynucleotides linked by phosphodiester linkages, and flanked on each side by a portion of modified DNA or RNA sequences. The flanking sequences include methyl phosphonate, phosphoromorpholidate, phosphoropiperazidate or phosphoramidate linkages.

U.S. Pat. No. 5,256,775, issued Oct. 26, 1993, describe mixed oligonucleotides that incorporate phosphoramidate linkages and phosphorothioate or phosphorodithioate linkages.

While it has been recognized that cleavage of a target RNA strand using an oligonucleotide and RNase H would be useful, nuclease resistance of the oligonucleotide and fidelity of hybridization are of great importance in the development of oligonucleotide therapeutics. Accordingly, there remains a long-felt need for methods and materials that could activate RNase H while concurrently maintaining or improving hybridization properties and providing nuclease resistance. Such oligonucleotides are also desired as research reagents and diagnostic agents.

BRIEF DESCRIPTION OF THE INVENTION

In accordance with one embodiment of this invention there are provided oligonucleotides formed from a sequence of nucleotide units. The oligonucleotides incorporate a least one nucleotide unit that is functionalized to increase nuclease resistance of the oligonucleotides. Further, at least some of the nucleotide units of the oligonucleotides are functionalized with a substituent group to increase binding affinity of the oligonucleotides to target RNAs, and at least some of the nucleotide units have 2'-deoxy-erythro-pentofuranosyl sugar moieties.

In preferred oligonucleotides of the present invention, nucleotide units which are functionalized for increased binding affinity are functionalized to include a 2'-substituent group. In preferred embodiments, the 2'-substituent group includes fluoro, $C_1$–$C_{20}$ alkoxy, $C_1$–$C_9$ aminoalkoxy, including aminopropoxy, allyloxy, imidazolylalkoxy and polyethylene glycol. Preferred alkoxy substituents include methoxy, ethoxy and propoxy. A preferred aminoalkoxy unit is aminopropoxy. A preferred imidazolylalkoxy substituent is imidazolylpropoxy.

In certain preferred oligonucleotides of the invention having increased nuclease resistance, each nucleotide unit of the oligonucleotides is linked by phosphorothioate linkages. In other preferred oligonucleotides, the 3' terminal nucleotide units are functionalized with 2' substituents.

The oligonucleotides include a plurality of nucleotide units bearing substituent groups that increase binding affinity of the oligonucleotide to a complementary strand of nucleic acid. In certain preferred embodiments, the nucleotide units that bear such substituents can be divided into a first nucleotide unit subsequence and a second nucleotide unit subsequence, with 2'-deoxy-erythro-pentofuranosyl-containing nucleotide units being positioned between the first nucleotide unit subsequence and the second nucleotide unit subsequence. It is preferred that all such intervening nucleotide units be 2'-deoxy-erythro-pentofuranosyl units.

In further preferred oligonucleotides of the invention, nucleotide units bearing substituents that increase binding affinity are located at one or both of the 3' or the 5' termini of the oligonucleotide. There can be from one to about eight nucleotide units that are substituted with substituent groups. Preferably, at least five sequential nucleotide units are 2'-deoxy-erythro-pentofuranosyl sugar moieties.

The present invention also provides macromolecules formed from a plurality of linked β-nucleosides including 2'-deoxy-erythro-pentofuranosyl β-nucleosides. These nucleosides are connected by linkages in a sequence that is hybridizable with a complementary nucleic acid. The linkages are selected from charged phosphorous linkages and non-phosphorous linkages. The sequence of linked nucleosides is divided into at least two regions. The first nucleoside region includes β-nucleosides linked by charged 3'–5' phosphorous linkages and β-nucleosides linked by non-phosphorous linkages. A second nucleoside region consists of 2'-deoxy-erythro-pentofuranosyl β-nucleosides linked by charged 3'–5' phosphorous linkages bearing a negative charge at physiological pH. In preferred embodiments, the macromolecules include at least 3 of said 2'-deoxy-erythro-pentofuranosyl β-nucleosides, more preferably at least 5 of said 2'-deoxy-erythro-pentofuranosyl β-nucleotides. In further preferred embodiments there exists a third nucleoside region whose nucleosides are selected from those selectable for the first region. In preferred embodiments the second region is positioned between the first and third regions. Such oligonucleotides of the present invention are also referred to as "chimeras," or "chimeric" or "gapped" oligonucleotides.

Preferred charged phosphorous linkages include phosphodiester, phosphorothioate and phosphorodithioate linkages; phosphodiester and phosphorothioate linkages are particularly preferred. Preferred non-phosphorous linkages include hydrazine linkages and hydroxylamine linkages.

Preferred nucleobases of the invention include adenine, guanine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, 5-uracil(pseudo uracil), 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine.

The invention also provides methods of treating an organism having a disease characterized by the undesired production of a protein. These methods include contacting the organism with an oligonucleotide having a sequence of nucleotides capable of specifically hybridizing with a complementary strand of nucleic acid with at least one of the nucleotides being functionalized to increase nuclease resistance of the oligonucleotide to nucleases, with a substituent group located thereon to increase binding affinity of the oligonucleotide to the complementary strand of nucleic acid, and with a plurality of the nucleotides have 2'-deoxy-erythro-pentofuranosyl sugar moieties.

Further in accordance with the present invention there are provided compositions including a pharmaceutically effective amount of an oligonucleotide having a sequence of nucleotides capable of specifically hybridizing with a complementary strand of nucleic acid having at least one of the nucleotides functionalized to increase nuclease resistance of the oligonucleotide to nucleases, wherein a plurality of the nucleotides have a substituent group located thereon to increase binding affinity of the oligonucleotide to the complementary strand of nucleic acid, and wherein a plurality of the nucleotides have 2'-deoxy-erythro-pentofuranosyl sugar moieties. The compositions further include a pharmaceutically acceptable diluent or carrier.

Further in accordance with this invention there are provided methods for in vitro modification of a sequence specific nucleic acid including contacting a test solution containing an RNase H enzyme and said nucleic acid with an oligonucleotide having a sequence of nucleotides capable of specifically hybridizing to a complementary strand of the nucleic acid, where at least one of the nucleotides is functionalized to increase nuclease resistance of the oligonucleotide to nucleases, where a plurality of the nucleotides have a substituent group located thereon to increase binding affinity of the oligonucleotide to the complementary strand of nucleic acid, and where a plurality of the nucleotides have 2'-deoxy-erythro-pentofuranosyl sugar moieties.

There are also provided methods of concurrently enhancing hybridization and RNase H enzyme activation in an organism that includes contacting the organism with an oligonucleotide having a sequence of nucleotides capable of specifically hybridizing to a complementary strand of nucleic acid, where at least one of the nucleotides is functionalized to increase nuclease resistance of the oligonucleotide to nucleases, where a plurality of the nucleotides have a substituent group located thereon to increase binding affinity of the oligonucleotide to the complementary strand of nucleic acid, and where a plurality of the nucleotides have 2'-deoxy-erythro-pentofuranosyl sugar moieties.

The invention further provides diagnostic methods for detecting the presence or absence of abnormal RNA molecules, or abnormal or inappropriate expression of normal RNA molecules in organisms or cells.

The compound was delivered by intravenous injected.

Figure 9:
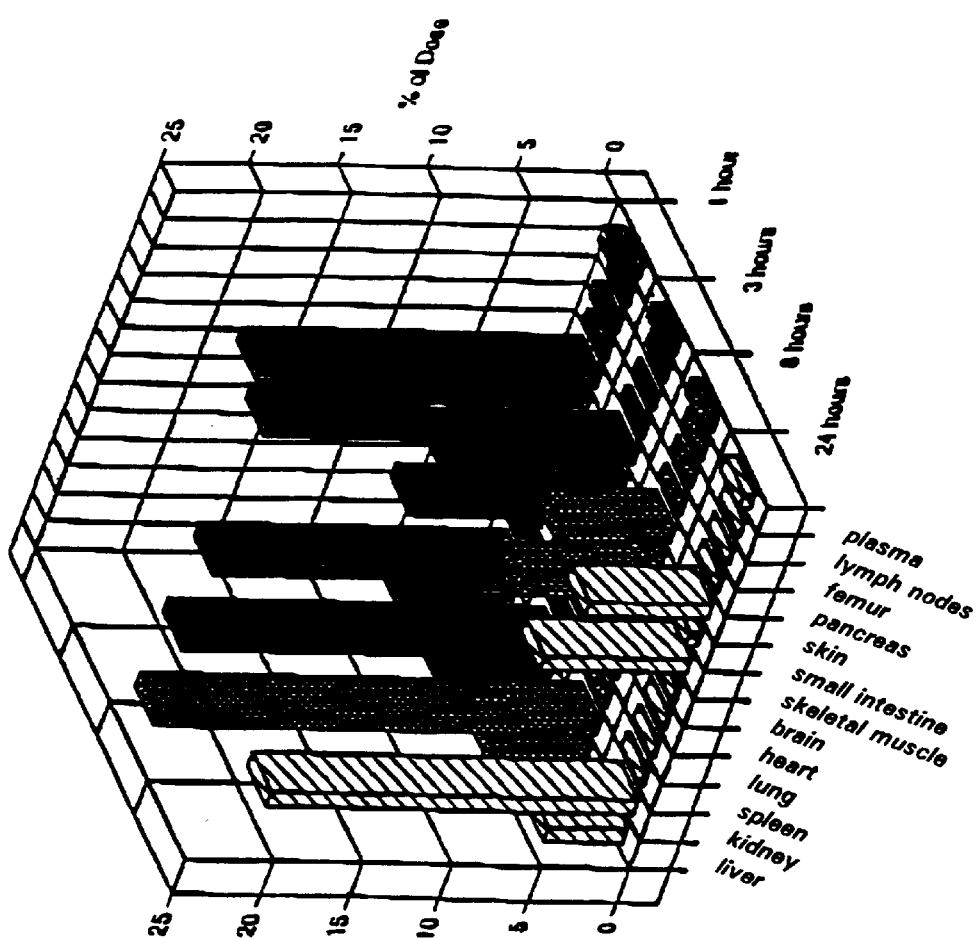

FIG. 9 is a three dimensional graph showing distribution of a further compound of the invention among various tissue in the mouse. Specific tissues are shown on one axis, time on a second axis and percent of dose on the third axis. The compound was delivered by intravenous injected.

DETAILED DESCRIPTION OF THE INVENTION

In accordance with the objects of this invention, novel oligonucleotides and macromolecules which have increased nuclease resistance, increased binding affinity to complementary strands of nucleic acids and that are substrates for RNase H are provided. The oligonucleotides and macromolecules of the invention are assembled from a plurality of nucleotide or nucleoside units. Each oligonucleotide or macromolecule of the invention includes at least one nucleotide or nucleoside unit that is functionalized to increase the nuclease resistance of the oligonucleotide. Further, in certain embodiments of the invention at least some of the nucleotide or nucleoside units bear a substituent group that increases the binding affinity of the oligonucleotide or macromolecule to a complementary strand of nucleic acid. Additionally, at least some of the nucleotide units comprise a 2'-deoxy-erythro-pentofuranosyl group as their sugar moiety.

In conjunction with the above guidelines, each nucleotide unit of an oligonucleotide of the invention, alternatively referred to as a subunit, can be a "natural" or a "synthetic" moiety. Thus, in the context of this invention, the term "oligonucleotide" refers to a polynucleotide formed from a plurality of joined nucleotide units. The nucleotide units are joined together via native internucleoside phosphodiester linkages. The nucleotide units are formed from naturally occurring nucleobases and pentofuranosyl sugar moieties. The term "oligonucleotide" thus effectively includes naturally occurring species or synthetic species formed from naturally occurring nucleotide units.

Oligonucleotides of the invention can also include modified subunits. The modifications can occur on the nucleobase portion of a nucleotide, on the sugar portion of a nucleotide or on the linkage joining one nucleotide to the next. In addition, nucleoside units can be joined via connecting groups that substitute for the internucleoside phosphate linkages. Macromolecules of the type have been identified as oligonucleosides. The term "oligonucleoside" thus refers to a plurality of nucleoside units joined by non-phosphorus linkages. In such oligonucleosides the linkages include an —O—CH$_2$—CH$_2$—O— linkage (i.e., an ethylene glycol linkage) as well as other novel linkages disclosed in U.S. Pat. No. 5,223,618, issued Jun. 29, 1993, U.S. Pat. No. 5,378,825, issued Jan. 3, 1995 and U.S. patent application Ser. No. 08/395,168, filed Feb. 27, 1995. Other modifications can be made to the sugar, to the base, or to the phosphate group of the nucleotide. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. 5,138,045, issued Aug. 11, 1992, all assigned to the assignee of this application. The disclosures of each of the above referenced publications are herein incorporated by reference.

Thus, in the context of the present invention, the term "oligonucleotide" is intended to include naturally occurring structures as well as non-naturally occurring or "modified" structures, including modified sugar moieties, modified base moieties or modified sugar linking moieties, that function similarly to natural bases, natural sugars and natural phosphodiester linkages. Thus, oligonucleotides can have altered base moieties, altered sugar moieties or altered intersugar linkages. Exemplary among these are phosphorothioate and phosphorodithioate internucleoside linkages used in place of phosphodiester internucleoside linkages, deaza or aza purines and pyrimidines used in place of natural purine and pyrimidine bases, pyrimidine bases having substituent groups at the 5 or 6 position, purine bases having altered or replacement substituent groups at the 2, 6 or 8 positions, or sugars having 2'-substituent groups. They may also comprise other modifications consistent with the spirit of this invention. Such oligonucleotides are best described as being functionally interchangeable with natural oligonucleotides (or synthetically prepared "natural" oligonucleotides), but which have one or more differences from the natural structure. All such oligonucleotides are comprehended by this invention so long as they function effectively in mimicking the structure of a desired RNA or DNA strand.

In one preferred embodiment of this invention, nuclease resistance is achieved by utilizing phosphorothioate internucleoside linkages. Contrary to the reports of Walder et al. noted above, I have found that in systems such as fetal calf serum containing a variety of 3'-exonucleases, modification of the internucleoside linkage from a phosphodiester linkage to a phosphorothioate linkage provides nuclease resistance.

Brill et al., *J. Am. Chem. Soc.* 1991, 113, 3972, reported that phosphorodithioate oligonucleotides also exhibit nuclease resistance. These authors also reported that phosphorodithioate oligonucleotides bind with complementary deoxyoligonucleotides, stimulate RNase H and stimulate the binding of lac repressor and cro repressor. In view of these properties, phosphorodithioates linkages also may be useful to increase nuclease resistance of oligonucleotides of the invention.

Nuclease resistance further can be achieved by locating a group at the 3'terminus of the oligonucleotide utilizing the methods of Saison-Behmoaras et al., supra, wherein a dodecanol group is attached to the 3' terminus of the oligonucleotide. Other suitable groups for providing increased nuclease resistance may include steroid molecules and other lipids, reporter molecules, conjugates and non-aromatic lipophilic molecules including alicyclic hydrocarbons, saturated and unsaturated fatty acids, waxes, terpenes and polyalicyclic hydrocarbons including adamantane and buckminsterfullerenes. Particularly useful as steroid molecules for this purpose are the bile acids including cholic acid, deoxycholic acid and dehydrocholic acid. Other steroids include cortisone, digoxigenin, testosterone and cholesterol and even cationic steroids such as cortisone having a trimethylaminomethyl hydrazide group attached via a double bond at the 3-position of the cortisone ring. Particularly useful reporter molecules are biotin and fluorescein dyes. Such groups can be attached to the 2'-hydroxyl group or 3'-hydroxyl group of the 3' terminal nucleotide either directly or utilizing an appropriate connector in the manner described in International Publication Number WO 93/07883, published Apr. 29, 1993, and assigned to the assignee of this application, the entire contents of which are herein incorporated by reference.

Attachment of functional groups at the 5' terminus of the compounds of the present invention also may contribute to nuclease resistance. Such groups include an acridine group (which also serves as an intercalator) or other groups that impart desirable pharmacokinetic or pharmacodynamic properties. Groups that impart pharmacodynamic properties, in the context of this invention, include groups that improve oligonucleotide uptake, enhance oligonucleotide resistance to degradation, and/or strengthened sequence-specific hybridization with RNA. Groups that impart pharmacokinetic properties, in the context of this invention, include groups that improve oligonucleotide uptake, distribution, metabolism or excretion.

Further nuclease resistance is expected to be conferred on oligonucleotides which utilize linkages such as an —O—CH$_2$—CH$_2$—O— linkage and similar linkages of the above identified U.S. Pat. No. 5,223,618, issued Jun. 29, 1993, U.S. No. 5,378,825, issued Jan. 3, 1995 and U.S. patent application Ser. No. 08/395,168, filed Feb. 27, 1995, since these types of linkages do not form a natural phosphodiester-containing backbone which is the natural substrate for nucleases. When nuclease resistance is conferred upon an oligonucleotide of the present invention by the use of a phosphorothioate or other nuclease resistant internucleotide linkage, such a linkage will reside at each internucleotide site. In other embodiments, less than all of the internucleotide linkages will be modified to a phosphorothioate or other nuclease resistant linkage.

I have found that the binding affinity of oligonucleotides of the present invention can be increased by incorporating substituent groups in the nucleotide subunits of the oligonucleotides of the invention. Preferred substituent groups are 2' substituent groups, i.e. substituent groups located at the 2' position of the sugar moiety of the nucleotide subunits of the oligonucleotides of the present invention. Presently preferred substituent groups include but are not limited to 2'-fluoro, 2'-alkoxy, 2'-aminoalkoxy, 2'-allyloxy, 2'-imidazolylalkoxy and 2'-polyethylene glycol. Alkoxy and aminoalkoxy groups generally include lower alkyl groups, particularly C$_1$–C$_9$ alkyl. Polyethylene glycols are of the structure (O—CH$_2$—CH$_2$)$_n$—O-alkyl. Particularly preferred substituent groups are 2'-fluoro, 2'-methoxy, 2'-ethoxy, 2'-propoxy, 2'-aminopropoxy, 2'-imidazolylpropoxy, 2'-imidazolylbutoxy, and 2'-allyloxy groups.

Binding affinity can also be increased by the use of certain modified nucleobases in the nucleotide units that make up the oligonucleotides of the invention. Such modified nucleobases may include 5-substituted pyrimidines, 6-azapyrimidines and N-2, N-6 and O-6 substituted purines, including 2-aminopropyladenine, 5-propynyluracil and 5-propynylcytosine. Other modified pyrimidine and purine bases are expected to increase the binding affinity of oligonucleotides to a complementary strand of nucleic acid.

The use of 2'-substituent groups increases the binding affinity of the substituted oligonucleotides of the present invention. In a published study (*Synthesis and Biophysical Studies of 2'-dRIBO-F Modified Oligonucleotides,* Conference On Nucleic Acid Therapeutics, Clearwater, Fla. Jan. 13, 1991), I have reported an increase in binding affinity of 1.6° C. per substituted nucleotide unit of a 15-mer phosphodiester oligonucleotide having 2'-fluoro substituent groups on five of the nucleotides of the oligonucleotide. When 11 of the nucleotides of the oligonucleotide bore 2'-fluoro substituent groups, the binding affinity increased to 1.8° C. per substituted nucleotide unit.

In the above-mentioned study, the 15-mer phosphodiester oligonucleotide was derivatized to the corresponding phosphorothioate analog. When the 15-mer phosphodiester oligonucleotide was compared to its phosphorothioate analog, the phosphorothioate analog had a binding affinity of only about 66% of that of the 15-mer phosphodiester oligonucleotide. Stated otherwise, binding affinity was lost in derivatizing the oligonucleotide to its phosphorothioate analog. However, when 2'-fluoro substituents were located on 11 of the nucleotides of the 15-mer phosphorothioate oligonucleotide, the binding affinity of the 2'-substituent groups more than overcame the decrease noted by derivatizing the 15-mer oligonucleotide to its phosphorothioate analog. In this compound, i.e. a 15-mer phosphorothioate oligonucleotide having 11 nucleotides substituted with 2'-fluoro substituent groups, the binding affinity was increased to 2.5° C. per substituent group. In this study no attempt was made to include an appropriate consecutive sequence of nucleotides having 2'-deoxy-erythro-pentofuranosyl sugars that would elicit RNase H enzymatic cleavage of a RNA target complementary to the oligonucleotide of the study.

In order to elicit RNase H enzymatic cleavage of a target RNA, an oligonucleotide of the invention must include a segment or subsequence therein that is a DNA-type segment. Stated otherwise, at least some of the nucleotide subunits of the oligonucleotides of the invention must have 2'-deoxy-erythro-pentofuranosyl sugar moieties. I have found that a subsequence having more than three consecutively linked 2'-deoxy-erythro-pentofuranosyl-containing nucleotide subunits is necessary in order to elicit RNase H activity upon hybridization with an oligonucleotide of the invention with a target RNA. It is presently preferred to have a subsequence of or more consecutive 2'-deoxy-erythro-pentofuranosyl containing nucleotide subunits in an oligonucleotide of the invention. Use of at least 7 consecutive 2'-deoxy-erythro-pentofuranosyl-containing nucleotide subunits is particularly preferred.

The mechanism of action of RNase H is recognition of a DNA-RNA duplex followed by cleavage of the RNA stand of this duplex. As noted in the Background section above, others in the art have used modified DNA strands to impart nuclease stability to the DNA strand. To do this they have used modified phosphate linkages which impart increased nuclease stability but detract from the hybridization properties. While I do not wish to be bound by theory, I have identified certain nucleosides or nucleoside analogs that will impart nuclease stability to an oligonucleotide, oligonucleoside or other macromolecule and in certain instances also lead to increased binding to a complementary strand of nucleic acid. These include β-nucleosides linked by charged 3'–5' linkages and β-nucleosides linked by non-phosphorous linkages.

Again, while not wishing to be bound by any particular theory, I have identified certain criteria which must be met for RNase H to recognize and elicit cleavage of an RNA strand. The first of these is that the RNA strand at the cleavage site must have its nucleoside units connected via a phosphate linkage that bears a negative charge. Additionally, the sugar moiety of the nucleosides at the cleavage site must be a β-pentofuranosyl sugar moiety and must also be in a 2' endo conformation. The only nucleosides (nucleotides) that fit this criteria are phosphodiester, phosphorothioate and phosphorodithioate nucleotides of 2'-deoxy-erythro-pentofuranosyl β-nucleosides.

Oligonucleosides having their nucleoside units connected via hydroxylamine and hydrazine linkages are prepared as per the published procedures by myself and co-authors in Vasseur et. al., *J. Am. Chem. Soc.* 1992, 114, 4006 and Debart 15 et. al., *Tetrahedron Letters* 1992, 33, 2645, as well as the disclosures of U.S. Pat. No. 5,378,825, issued Jan. 3, 1995, and U.S. Pat. No. 5,386,023, issued Jan. 31, 1995, both of which are commonly assigned with this application, the entire contents of which are herein incorporated by reference.

Further, non-phosphate linkages suitable for use in this invention include linkages which have two adjacent heteroatoms in combination with one or two methylene moieties. Oligonucleosides having their nucleosides connected by such linkages are prepared as per International Publication Number WO 94/00467, published Jan. 6, 1994, the entire contents of which are herein incorporated by reference.

For use in preparing such structural units, suitable nucleobases include adenine, guanine, cytosine, uracil, thymine, xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thiolalkyl, hydroxyl and other 8-substituted adenines and guanines, 5-trifluoromethyl and other 5-substituted uracils and cytosines, 7-methylguanine and other nucleobases such as those disclosed in U.S. Pat. No. 3,687,808, issued Aug. 29, 1972.

The oligonucleotides and macromolecules of the invention preferably comprise from about 10 to about 30 nucleotide or nucleobase subunits. It is more preferred that such oligonucleotides and macromolecules comprise from about 15 to about 25 subunits. As will be appreciated, a "subunit" is a nucleobase and sugar combination suitably bound to adjacent subunits through phosphorus or non-phosphorus linkages. The term "subunit" is used interchangeably with the term "unit." In order to elicit an RNase H response, as specified above, within this total overall sequence length of the oligonucleotide or macromolecule will be a subsequence of greater than three, but preferably five or more, consecutively linked 2'-deoxy-erythro-pentofuranosyl-containing nucleotide subunits.

It is presently preferred to incorporate the 2'-deoxy-erythro-pentofuranosyl-containing nucleotide subsequence in the oligonucleotide or macromolecule such that within the oligonucleotide or macromolecule other nucleotide subunits of the oligonucleotide or macromolecule are located on either side of the 2'-deoxy-erythro-pentofuranosyl nucleotide subsequence.

In certain embodiments of the invention, if the remainder of the nucleotide subunits each include a 2'-substituent group for increased binding affinity, then the 2'-deoxy-erythro-pentofuranosyl nucleotide subsequence will be located between a first subsequence of nucleotide subunits having 2'-substituent groups and a second subsequence of nucleotide subunits having 2'-substituent groups. Other constructions are also possible, including locating the 2'-deoxy-erythro-pentofuranosyl nucleotide subsequence at either the 3' or the 5' terminus of the oligonucleotides of the present invention.

Compounds of the invention can be utilized as diagnostics, therapeutics and as research reagents and kits. They can be utilized in pharmaceutical compositions by adding an effective amount of an oligonucleotide of the invention to a suitable pharmaceutically acceptable diluent or carrier. They further can be used for treating organisms having a disease characterized by the undesired production of a protein. The organism can be contacted with an oligonucleotide of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, in doses ranging from 0.01 μg to 100 g per kg of body weight depending on the age of the patient and the severity of the disease state being treated. Further, the treatment regimen may last for a period of time which will vary depending upon the nature of the particular disease, its severity and the overall condition of the patient, and may extend from once to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomer of the invention in conjunction with other traditional therapeutic modalities. For example, a patient being treated for AIDS may be administered an oligomer in conjunction with AZT, or a patient with atherosclerosis may be treated with an oligomer of the invention following angioplasty to prevent reocclusion of the treated arteries.

Following successful treatment, it may be desirable to have the patient undergo maintenance therapy to prevent the recurrence of the disease state, wherein the oligomer is administered in maintenance doses, ranging from 0.01 µg to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}s$ found to be effective in in vitro and in vivo animal models. In general, dosage is from 0.01 µg to 100 g per kg of body weight, and may be given once or more daily, weekly, monthly or yearly, or even once every 2 to 20 years.

Such therapeutic treatment can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular machinery is susceptible to such therapeutic and/or prophylactic treatment. Seemingly diverse organisms such as bacteria, yeast, protozoa, algae, plant and higher animal forms, including warm-blooded animals, can be treated in this manner. Further, since each of the cells of multicellular eukaryotes also includes both DNA-RNA transcription and RNA-protein translation as an integral part of their cellular activity, such therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations or organelles also can be included within the definition of organisms that are capable of being treated with the therapeutic or diagnostic oligonucleotides of the invention. As used herein, therapeutics is meant to include both the eradication of a disease state, killing of an organism, e.g. bacterial, protozoan or other infection, or control of aberrant or undesirable cellular growth or expression.

In the context of this invention, "hybridization" shall mean hydrogen bonding, which may be Watson-Crick, Hoogsteen or reversed Hoogsteen hydrogen bonding, between complementary nucleotide units. For example, adenine and thymine are complementary nucleobases which pair through the formation of hydrogen bonds. "Complementary," as used herein, also refers to subunit sequence complementarity between two nucleotide units. For example, if a nucleotide unit at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity such that stable and specific binding occurs between the oligonucleotide and the DNA or RNA target. It is understood that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a loss of utility, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

For the purpose of illustration, the compounds of the invention have been used in a ras-luciferase fusion system using ras-luciferase transactivation. As described in International Publication Number WO 92/22651, published Dec. 23, 1992 and commonly assigned with this application, the entire contents of which are herein incorporated by reference, the ras oncogenes are members of a gene family that encode related proteins that are localized to the inner face of the plasma membrane. Ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The most commonly detected activating ras mutation found in human tumors is in codon-12 of the H-ras gene in which a base change from GGC to GTC results in a glycine-to-valine substitution in the GTPase regulatory domain of the ras protein product. This single amino acid change is thought to abolish normal control of ras protein function, thereby converting a normally regulated cell protein to one that is continuously active. It is believed that such deregulation of normal ras protein function is responsible for the transformation from normal to malignant growth.

The oligonucleotides of the present invention have also been used for modulating the expression of the raf gene, a naturally present cellular gene which occasionally converts to an activated form that has been implicated in abnormal cell proliferation and tumor formation.

The oligonucleotides of the present invention are also specifically hybridizable with nucleic acids relating to protein kinase C (PKC). These oligonucleotides have been found to modulate the expression of PKC.

The following examples and procedures illustrate the present invention and are not intended to limit the same.

EXAMPLE 1

Oligonucleotide Synthesis

Unsubstituted and substituted oligonucleotides were synthesized on an automated DNA synthesizer (Applied Biosystems model 380B) using standard phosphoramidite chemistry with oxidation by iodine. For phosphorothioate oligonucleotides, the standard oxidation bottle was replaced by 0.2 M solution of 3H-1,2-benzodithiole-3-one 1,1-dioxide in acetonitrile for the step wise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution. Analytical gel electrophoresis was accomplished in 20% acrylamide, 8 M urea, 454 mM Tris-borate buffer, pH=7.0. Oligonucleotides and phosphorothioates were judged, based on polyacrylamide gel electrophoresis, to be greater than 80% full-length material.

EXAMPLE 2

Oligonucleotide Having 2'-Substituted Oligonucleotides Regions Flanking Central 2'-Deoxy Phosphorothioate Oligonucleotide Region A 15-mer RNA target of the sequence 5' GCG TTT TTT TTT TGC G 3' was prepared in the normal manner on the DNA sequencer using RNA protocols. A series of complementary phosphorothioate oligonucleotides having 2'-O-substituted nucleotides in regions that flank a 2'-deoxy region were prepared utilizing 2'-O-substituted nucleotide precursors prepared as per known literature preparations, i.e. 2'-O-methyl, or as per the procedure of International Publication Number WO 92/03568, published Mar. 5, 1992. The 2'-O-substituted nucleotides were added as their 5'-O-dimethoxytrityl-3'-phosphoramidites in the normal manner on the DNA synthesizer. The complementary oligonucleotides have the sequence of 5' CGCAAAAAAAAAAAAACGC 3' (SEQ ID NO:28). The 2'-O-substituent was located in CGC and CG regions of these oligonucleotides. The following 2'-O-substituents were used: 2'-fluoro; 2'-O-methyl; 2'-O-propyl; 2'-O-allyl; 2'-O-aminopropoxy; 2'-O-(methoxyethoxyethyl), 2'-O-imidazolebutoxy and 2'-O-imidazolepropoxy.

EXAMPLE 3

Ras-Luciferase Reporter Gene Assembly

The ras-luciferase reporter genes described in this study were assembled using PCR technology. Oligonucleotide primers were synthesized for use as primers for PCR cloning of the 5'-regions of exon 1 of both the mutant (codon 12) and non-mutant (wild-type) human H-ras genes. H-ras gene templates were purchased from the American Type Culture Collection (ATCC numbers 41000 and 41001) in Bethesda, Md. The oligonucleotide PCR primers 5'-ACA-TTA-TGC-TAG-CTT-TTT-GAG-TAA-ACT-TGT-GGG-GCA-GGA-GAC-CCT-GT-3' (sense), SEQ ID NO: 15, and 5'-GAG-ATC-TGA-AGC-TTC-TGG-ATG-GTC-AGC-GC-3' (antisense), SEQ ID NO: 16, were used in standard PCR reactions using mutant and non-mutant H-ras genes as templates. These primers are expected to produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the P. pyralis (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were 5'-GAG-ATC-TGA-AGC-TTG-AAG-ACG-CCA-AAA-ACA-TAA-AG-3' (sense), SEQ ID NO: 17, and 5'-ACG-CAT-CTG-GCG- CGC-CGA-TAC-CGT-CGA-CCT-CGA-3' (antisense), SEQ ID NO: 18, were used in standard PCR reactions using a commercially available plasmid (pT3/T7-Luc) (Clontech), containing the luciferase reporter gene, as a template. These primers were expected to yield a product of approximately 1.9 kb corresponding to the luciferase gene, flanked by HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter.

EXAMPLE 4

Transfection of Cells with Plasmid DNA

Transfections were performed as described by Greenberg (Current Protocols in Molecular Biology, Ausubel et al., eds.), John Wiley and Sons, New York), with the following modifications: HeLa cells were plated on 60 mm dishes at 5×10$^5$ cells/dish. A total of 10 μg of DNA was added to each dish, of which 9 μg was ras-luciferase reporter plasmid and 1 μg was a vector expressing the rat glucocorticoid receptor under control of the constitutive Rous sarcoma virus (RSV) promoter. Calcium phosphate-DNA coprecipitates were removed after 16–20 hours by washing with Tris-buffered saline [50 Mm Tris-Cl (pH 7.5), 150 mM NaCl] containing 3 mM EGTA. Fresh medium supplemented with 10% fetal bovine serum was then added to the cells. At this time, cells were pre-treated with antisense oligonucleotides prior to activation of reporter gene expression by dexamethasone.

EXAMPLE 5

Oligonucleotide Treatment of Cells

Immediately following plasmid transfection, cells were thrice washed with OptiMEM (GIBCO), and prewarmed to 37° C. 2 ml of OptiMEM containing 10 μg/ml N-[1-(2,3-dioleyloxy)propyl]-N,N,N,-trimethylammonium chloride (DOTMA) (Bethesda Research Labs, Gaithersburg, Md.) was added to each dish and oligonucleotides were added directly and incubated for 4 hours at 37° C. OptiMEM was then removed and replaced with the appropriate cell growth medium containing oligonucleotide. At this time, reporter gene expression was activated by treatment of cells with dexamethasone to a final concentration of 0.2 μM. Cells were harvested 12–16 hours following steroid treatment.

EXAMPLE 6

Luciferase Assays

Luciferase was extracted from cells by lysis with the detergent Triton X-100, as described by Greenberg (Current Protocols in Molecular Biology, Ausubel et al., eds., John Wiley and Sons, New York). A Dynatech ML1000 luminometer was used to measure peak luminescence upon addition of luciferin (Sigma) to 625 μM. For each extract, luciferase assays were performed multiple times, using differing amounts of extract to ensure that the data were gathered in the linear range of the assay.

EXAMPLE 7

Antisense Oligonucleotide Inhibition of ras-Luciferase Gene Expression

A series of antisense phosphorothioate oligonucleotide analogs targeted to the codon-12 point mutation of activated H-ras were tested using the ras-luciferase reporter gene system described in the foregoing examples. This series comprised a basic sequence and analogs of that basic sequence. The basic sequence was of known activity as reported in International Publication Number WO 92/22651 identified above. In both the basic sequence and its analogs, each of the nucleotide subunits incorporated phosphorothioate linkages to provide nuclease resistance. Each of the analogs incorporated nucleotide subunits that contained 2'-O-methyl substitutions and 2'-deoxy-erythro-pentofuranosyl sugars. In the analogs, a subsequence of the 2'-deoxy-erythro-pentofuranosyl sugar-containing subunits was flanked on both ends by subsequences of 2'-O-methyl substituted subunits. The analogs differed from one another with respect to the length of the subsequence of the 2'-deoxy-erythro-pentofuranosyl sugar containing nucleotides. The length of these subsequences varied by 2 nucleotides between 1 and 9 total nucleotides. The 2'-deoxy-erythro-pentofuranosyl nucleotide sub-sequences were centered at the point mutation of the codon-12 point mutation of the activated ras.

The base sequences, sequence reference numbers and sequence ID numbers of these oligonucleotides (all are phosphorothioate analogs) are shown in Table 1. In this table those nucleotides identified with a "$^M$" contain a 2'-O-methyl substituent group and the remainder of the nucleotides identified with a "$_d$" are 2'-deoxy-erythro-pentofuranosyl nucleotides.

TABLE 1

Chimeric 2'-O-methyl P = S oligonucleotides

| OLIGO | SEQUENCE | | | | | | SEQ ID NO. |
|---|---|---|---|---|---|---|---|
| 2570 | $C_dC_dA_d$ | $C_dA_dC_d$ | $C_dG_dA_d$ | $C_dG_dG_d$ | $C_dG_dC_d$ | $C_dC_d$ | 1 |
| 3975 | $C^MC^MA^M$ | $C^MA^MC^M$ | $C^MG^MA_d$ | $C^MG^MG^M$ | $C^MG^MC^M$ | $C^MC^M$ | 1 |
| 3979 | $C^MC^MA^M$ | $C^MA^MC^M$ | $C^MG_dA_d$ | $C_dG^MG^M$ | $C^MG^MC^M$ | $C^MC^M$ | 1 |
| 3980 | $C^MC^MA^M$ | $C^MA^MC^M$ | $C_dG_dA_d$ | $C_dG_dG^M$ | $C^MG^MC^M$ | $C^MC^M$ | 1 |
| 3985 | $C^MC^MA^M$ | $C^MA^MC_d$ | $C_dG_dA_d$ | $C_dG_dG_d$ | $C^MG^MC^M$ | $C^MC^M$ | 1 |
| 3984 | $C^MC^MA^M$ | $C^MA_dC_d$ | $C_dG_dA_d$ | $C_dG_dG_d$ | $C_dG^MC^M$ | $C^MC^M$ | 1 |

Figure 1:
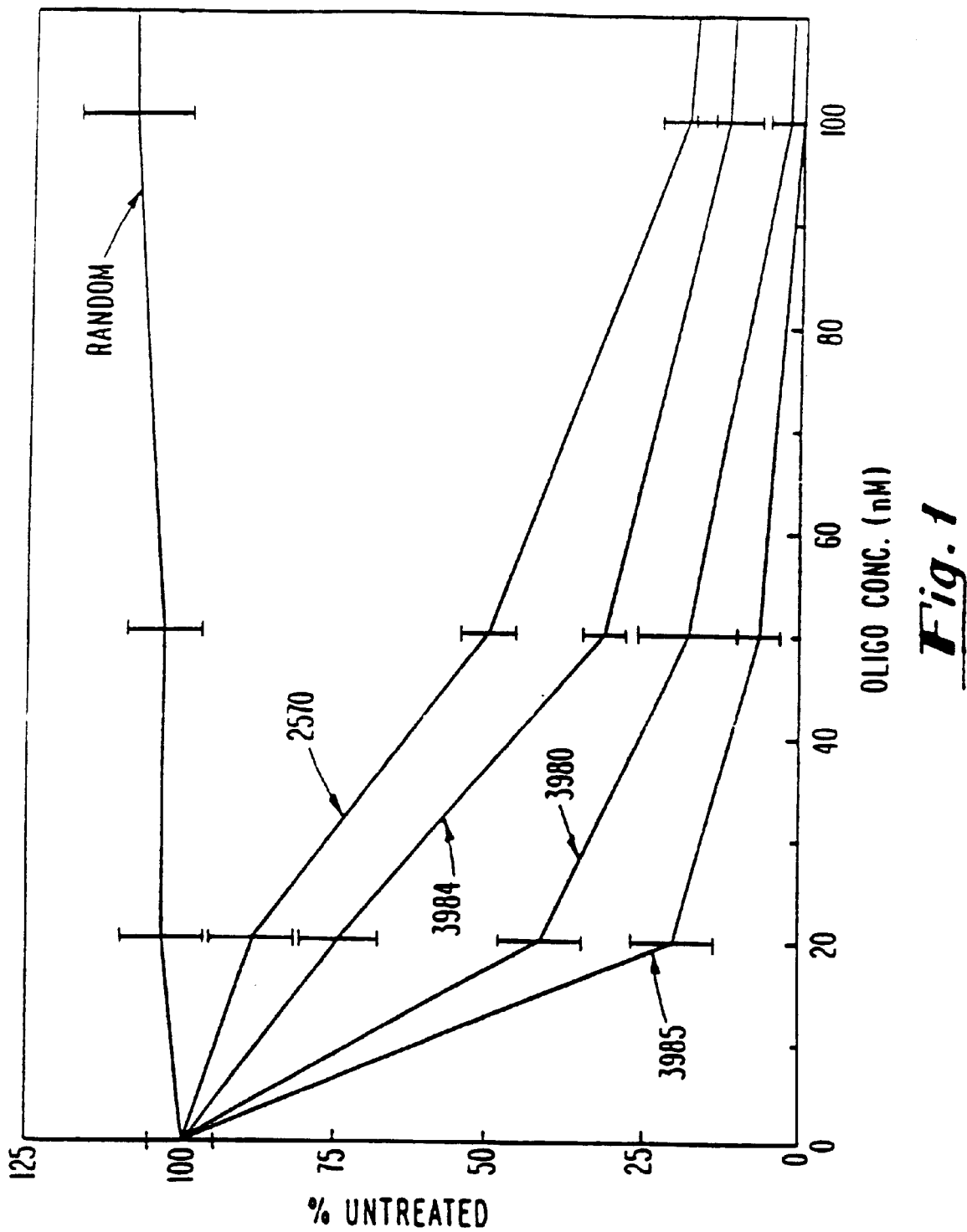
FIG. 1 is a graph showing dose response activity of oligonucleotides of the invention and a reference compound.

FIG. 1 shows dose-response data in which cells were treated with the phosphorothioate oligonucleotides of Table 1. Oligonucleotide 2570 is targeted to the codon-12 point mutation of mutant (activated) H-ras RNA. The other nucleotides have 2'-O-methyl substituents groups thereon to increase binding affinity with sections of various lengths of interspaced 2'-deoxy-erythro-pentofuranosyl nucleotides. The control oligonucleotide is a random phosphorothioate oligonucleotide analog, 20 bases long. Results are expressed as percentage of luciferase activity in transfected cells not treated with oligonucleotide. As the figure shows, treatment of cells with increasing concentrations of oligonucleotide 2570 resulted in a dose-dependent inhibition of ras-luciferase activity in cells expressing the mutant form of ras-luciferase. Oligonucleotide 2570 displays an approximate threefold selectivity toward the mutant form of ras-luciferase as compared to the normal form.

As is further seen in FIG. 1, each of the oligonucleotides 3980, 3985 and 3984 exhibited greater inhibition of ras-luciferase activity than did oligonucleotide 2570. The greatest inhibition was displayed by oligonucleotide 3985 that has a subsequence of 2'-deoxy-erythro-pentofuranosyl nucleotides seven nucleotides long. Oligonucleotide 3980, having a five nucleotide long 2'-deoxy-erythro-pentofuranosyl nucleotide subsequence exhibited the next greatest inhibition followed by oligonucleotide 3984 that has a nine nucleotide 2'-deoxy-erythro-pentofuranosyl nucleotide subsequence.

Figure 2:
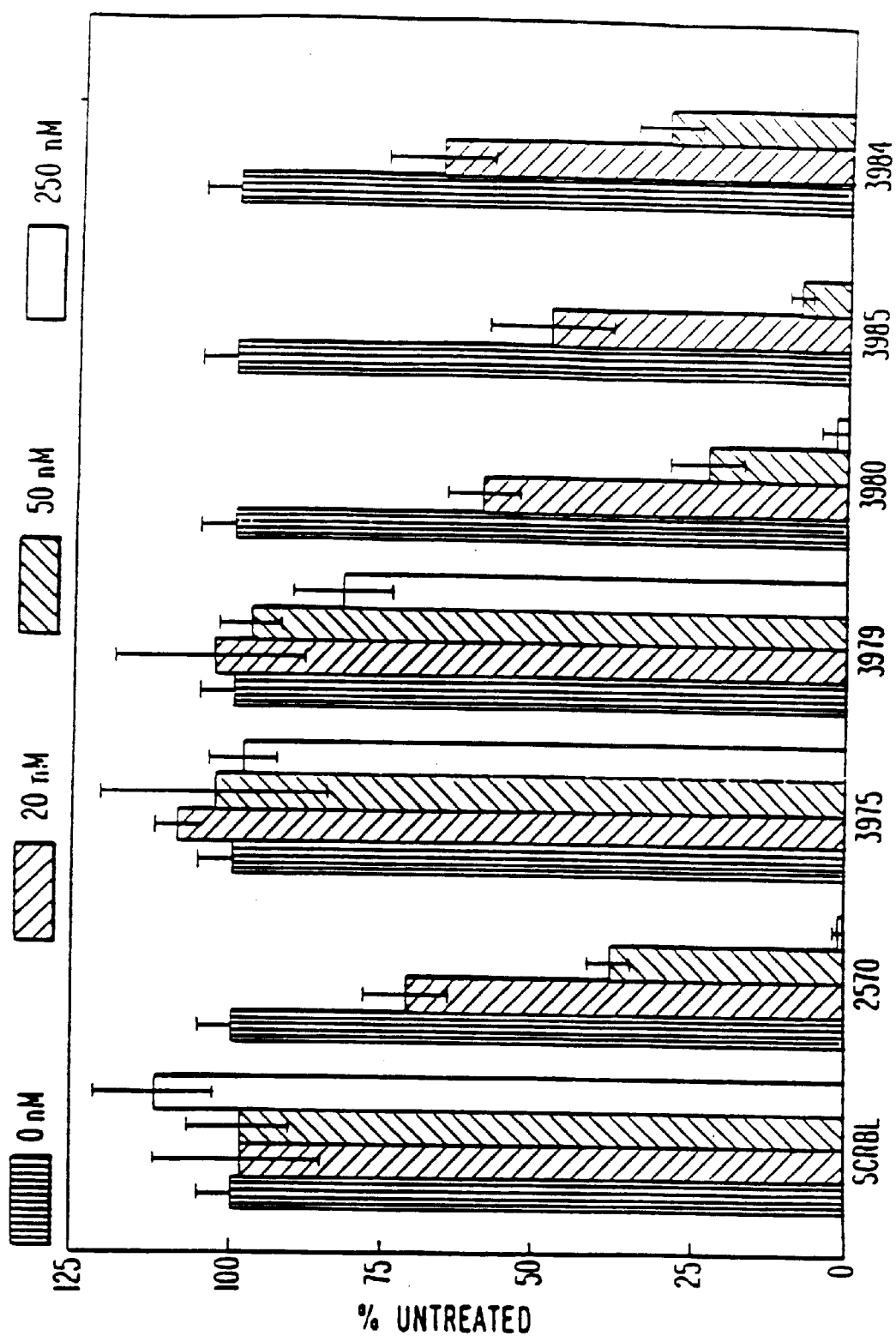
FIG. 2 is a bar chart showing dose response activity of oligonucleotides of the invention and reference compounds.

FIG. 2 shows the results similar to FIG. 1 except it is in bar graph form. Further seen on FIG. 2 is the activity of oligonucleotide 3975 and oligonucleotide 3979. These oligonucleotides have subsequences of 2'-deoxy-erythro-pentofuranosyl nucleotides one and three nucleotides long, respectively. As is evident from FIG. 2, neither of the oligonucleotides having either the one or the three 2'-deoxy-erythro-pentofuranosyl nucleotide subsequences showed significant activity. There was measurable activity for the three nucleotide subsequence oligonucleotide 3979 at the highest concentration dose.

The increases in activity of oligonucleotides 3980, 3985 and 3984 compared to oligonucleotide 2570 is attributed to the increase in binding affinity imparted to these compounds by the 2'-O-methyl substituent groups located on the compounds and by the RNase H activation imparted to these compounds by incorporation of a subsequence of 2'-deoxy-erythro-pentofuranosyl nucleotides within the main sequence of nucleotides. In contrast to the active compounds of the invention, it is interesting to note that sequences identical to those of the active oligonucleotides 2570, 3980, 3985 and 3984 but having phosphodiester linkages in stead of the phosphorothioate linkages of the active oligonucleotides of the invention showed no activity. This is attributed to these phosphodiester compounds being substrates for nucleases that degrade such phosphodiester compounds thus preventing them potentially activating RNase H.

Other Sugar Modifications

The effects of other 2' sugar modifications besides 2'-O-methyl on antisense activity in chimeric oligonucleotides have been examined. These modifications are listed in Table 2, along with the $T_m$ values obtained when 17-mer oligonucleotides having 2'-modified nucleotides flanking a 7-base deoxy gap were hybridized with a 25-mer oligoribonucleotide complement as described in Example 8. A relationship was observed for these oligonucleotides between alkyl length at the 2' position and $T_m$. As alkyl length increased, $T_m$ decreased. The 2'-fluoro chimeric oligonucleotide displayed the highest $T_m$ of the series.

TABLE 2

Correlation of $T_m$ with Antisense Activity
2'-modified 17-mer with 7-deoxy gap
CCACACCGACGGCGCCC (SEQ ID NO: 1)

| 2' MODIFICATION | $T_m$ (°C.) | $IC_{50}$ (nM) |
|---|---|---|
| Deoxy | 64.2 | 150 |
| O-Pentyl | 68.5 | 150 |
| O-Propyl | 70.4 | 70 |
| O-Methyl | 74.7 | 20 |
| Fluoro | 76.9 | 10 |

These 2' modified oligonucleotides were tested for antisense activity against H-ras using the transactivation reporter gene assay described in Example 9. All of these 2' modified chimeric compounds inhibited ras expression, with the 2'-fluoro 7-deoxy-gap compound being the most active. A 2'-fluoro chimeric oligonucleotide with a centered 5-deoxy gap was also active.

Chimeric phosphorothioate oligonucleotides having SEQ ID NO: 1 having 2'-O-propyl regions surrounding a 5-base or 7-base deoxy gap were compared to 2'-O-methyl chimeric oligonucleotides. ras expression in T24 cells was inhibited by both 2'-O-methyl and 2'-O-propyl chimeric oligonucleotides with a 7-deoxy gap and a uniform phosphorothioate backbone. When the deoxy gap was decreased to five nucleotides, only the 2'-O-methyl oligonucleotide inhibited ras expression.

Antisense Oligonucleotide Inhibition of H-ras Gene Expression in Cancer Cells

Two phosphorothioate oligonucleotides (2502, 2503) complementary to the ras AUG region were tested as described in Example 10, along with chimeric oligonucleotides (4998, 5122) having the same sequence and 7-base deoxy gaps flanked by 2'-O-methyl regions. These chimeric oligonucleotides are shown in Table 3.

TABLE 3

Chimeric phosphorothioate oligonucleotides
having 2'-O-methyl ends (bold) and central deoxy
gap (AUG target)

| OLIGO | # DEOXY | SEQUENCE | SEQ ID NO. |
|---|---|---|---|
| 2502 | 20 | CTTATATTCCGTCATCGCTC | 2 |
| 4998 | 7 | CTTATATTCCGTCATCGCTC | 2 |

TABLE 3-continued

Chimeric phosphorothioate oligonucleotides
having 2'-O-methyl ends (bold) and central deoxy
gap (AUG target)

| OLIGO | # DEOXY | SEQUENCE | SEQ ID NO. |
|---|---|---|---|
| 2503 | 20 | TCCGTCATCGCTCCTCAGGG | 3 |
| 5122 | 7 | TCCGTCATCGCTCCTCAGGG | 3 |

Compound 2503 inhibited ras expression in T24 cells by 71%, and the chimeric compound (4998) inhibited ras mRNA even further (84% inhibition). Compound 2502, also complementary to the AUG region, decreased ras RNA levels by 26% and the chimeric version of this oligonucleotide (5122) demonstrated 15% inhibition. Also included in this assay were two oligonucleotides targeted to the mutant codon 12. Compound 2570 (SEQ ID NO: 1) decreased ras RNA by 82% and the 2'-O-methyl chimeric version of this oligonucleotide with a seven-deoxy gap (3985) decreased ras RNA by 95%.

Oligonucleotides 2570 and 2503 were also tested to determine their effects on ras expression in HeLa cells, which have a wild-type (i.e., not activated) H-ras codon 12. While both of these oligonucleotides inhibited ras expression in T24 cells (having activated codon 12), only the oligonucleotide (2503) specifically hybridizable with the ras AUG inhibited ras expression in HeLa cells. Oligonucleotide 2570 (SEQ ID NO: 1), specifically hybridizable with the activated codon 12, did not inhibit ras expression in HeLa cells, because these cells lack the activated codon-12 target.

Oligonucleotide 2570, a 17-mer phosphorothioate oligonucleotide complementary to the codon 12 region of activated H-ras, was tested for inhibition of ras expression (as described in Example 8) in T24 cells along with chimeric phosphorothioate 2'-O-methyl oligonucleotides 3980, 3985 and 3984, which have the same sequence as 2570 and have deoxy gaps of 5, 7 and 9 bases, respectively (shown in Table 1). The fully 2'-deoxy oligonucleotide 2570 and the three chimeric oligonucleotides decreased ras mRNA levels in T24 cells. Compounds 3985 (7-deoxy gap) and 3984 (9-deoxy gap) decreased ras mRNA by 81%; compound 3980 (5-deoxy gap) decreased ras mRNA by 61%. Chimeric oligonucleotides having this sequence, but having 2'-fluoro-modified nucleotides flanking a 5-deoxy (4689) or 7-deoxy (4690) gap, inhibited ras mRNA expression in T24 cells, with the 7-deoxy gap being preferred (82% inhibition, vs 63% inhibition for the 2'-fluoro chimera with a 5-deoxy gap).

Antisense Oligonucleotide Inhibition of Proliferation of Cancer Cells

Three 17-mer oligonucleotides having the same sequence (SEQ ID NO: 1), complementary to the codon 12 region of activated ras, were tested for effects on T24 cancer cell proliferation as described in Example 11. 3985 is a full phosphorothioate having a 7-deoxy gap flanked by 2'-O-methyl nucleotides, and 4690 is a full phosphorothioate having a 7-deoxy gap flanked by 2'-F nucleotides ($C^F C^F A^F C^F A^F C_d C_d G_d A_d C_d G_d G_d C^F G^F C^F C^R C^F$, SEQ. ID NO. 1, nucleotides identified with an "$^F$" contain a 2'-O-fluoro substituent group and the remainder of the nucleotides identified with a "$_d$" are 2'-deoxy-erythro-pentofuranosyl nucleotides). Effects of these oligonucleotides on cancer cell proliferation correlated well with their effects on ras mRNA expression shown by Northern blot analysis: oligonucleotide 2570 inhibited cell proliferation by 61%, the 2'-O-methyl chimeric oligonucleotide 3985 inhibited cell proliferation by 82%, and the 2'-fluoro chimeric analog inhibited cell proliferation by 93%.

In dose-response studies of these oligonucleotides on cell proliferation, the inhibition was shown to be dose-dependent in the 25 nM–100 nM range. $IC_{50}$ values of 44 nM, 61 nM and 98 nM could be assigned to oligonucleotides 4690, 3985 and 2570, respectively. The random oligonucleotide control had no effect at the doses tested.

The effect of ISIS 2570 on cell proliferation was cell type-specific. The inhibition of T24 cell proliferation by this oligonucleotide was four times as severe as the inhibition of HeLa cells by the same oligonucleotide (100 nM oligonucleotide concentration). ISIS 2570 is targeted to the activated (mutant) ras codon 12, which is present in T24 but lacking in HeLa cells, which have the wild-type codon 12.

Chimeric Backbone-Modified Oligonucleotides

Oligonucleotides discussed in previous examples have had uniform phosphorothioate backbones. The 2'modified chimeric oligonucleotides discussed above are not active in uniform phosphodiester backbones. A chimeric oligonucleotide was synthesized (ISIS 4226) having 2'-O-methyl regions flanking a 5-nucleotide deoxy gap, with the gap region having a P=S backbone and the flanking regions having a P=O backbone. Another chimeric oligonucleotide (ISIS 4223) having a P=O backbone in the gap and P=S in flanking regions was also made. These oligonucleotides are shown in Table 4.

Additional oligonucleotides were synthesized, completely 2'deoxy and having phosphorothioate backbones containing either a single phosphodiester (ISIS 4248), two phosphodiesters (ISIS 4546), three phosphodiesters (ISIS 4551), four phosphodiesters (ISIS 4593), five phosphodiesters (ISIS 4606) or ten phosphodiester linkages (ISIS-4241) in the center the molecule. These oligonucleotides are also shown in Table 4.

TABLE 4

Chimeric backbone (P = S/P = O) oligonucleotides having 2'-O-methyl wings (bold) and central deoxy gap (backbone linkages indicated by s (P = S) or o (P = O)

| OLIGO | # P = S | SEQUENCE | SEQ ID NO. |
|---|---|---|---|
| 2570 | 16 | CsCsAsCsAsCsCsGsAsCsGsGsCsGsCsC | 1 |
| 4226 | 5 | CoCoAoCoAoCsCsGsAsCsGoGoCoGoCoCoC | 1 |
| 4233 | 11 | CsCsAsCsAsCoCoGoAoCoGsGsCsGsCsCsC | 1 |
| 4248 | 15 | CsCsAsCsAsCsCsGsAoCsGsGsCsGsCsC | 1 |
| 4546 | 14 | CsCsAsCsAsCsGoAoCsGsGsCsGsCsCsC | 1 |
| 4551 | 13 | CsCsAsCsAsCsGoAoCoGsGsCsGsCsCsC | 1 |
| 4593 | 12 | CsCsAsCsAsCoGoAoCoGsGsCsGsCsCsC | 1 |
| 4606 | 11 | CsCsAsCsAsCoGoAoCoGoGsCsGsCsCsC | 1 |
| 4241 | 6 | CsCsAsCoAoCoCoGoAoCoGoGoCoGsCsC | 1 |

Oligonucleotides were incubated in crude HeLa cellular extracts at 37° C. to determine their sensitivity to nuclease degradation as described in Dignam et al., *Nucleic Acids Res.* 11, 1475–1489. The oligonucleotide (4233) with a five-diester gap between phosphorothioate/2'-O-methyl wings had a $T_{1/2}$ of 7 hr. The oligonucleotide with a five-phosphorothioate gap in a phosphorothioate/2'-O-methyl molecule had a $T_{1/2}$ of 30 hours. In the set of oligonucleotides having one to ten diester linkages, the oligonucleotide (4248) with a single phosphodiester linkage was as stable to nucleases as was the full-phohosphorothioate molecule, ISIS 2570, showing no degradation after 5 hours in HeLa cell extract. Oligonucleotides with two-, three and four-diester gaps had $T_{1/2}$ of approximately 5.5 hours, 3.75 hours, and 3.2 hours, and oligonucleotides with five or ten deoxy linkages had $T_{1/2}$ of 1.75 hours and 0.9 hours, respectively.

Antisense Activity of Chimeric Backbone-Modified Oligonucleotides

A uniform phosphorothioate backbone is not required for antisense activity. ISIS 4226 and ISIS 4233 were tested in the ras-luciferase reporter system for effect on ras expression along with ISIS 2570 (fully phosphorothioate/all deoxy), ISIS 3980 (fully phosphorothioate, 2'-O-methyl wings with deoxy gap) and ISIS 3961 (fully phosphodiester, 2'-O-methyl wings with deoxy gap). All of the oligonucleotides having a P=S (i.e., nuclease-resistant) gap region inhibited ras expression. The two completely 2'deoxy oligonucleotides having phosphorothioate backbones containing either a single phosphodiester (ISIS 4248) or ten phosphodiester linkages (ISIS 4241) in the center of the molecule were also assayed for activity. The compound containing a single P=O was just as active as a full P=S molecule, while the same compound containing ten P=O was completely inactive.

Chimeric phosphorothioate oligonucleotides of SEQ ID NO: 1 were made, having a phosphorothioate backbone in the 7-base deoxy gap region only, and phosphodiester in the flanking regions, which were either 2'-O-methyl or 2'-O-propyl. The oligonucleotide with the 2'-O-propyl diester flanking regions was able to inhibit ras expression.

EXAMPLE 8

Melting Curves

Absorbance vs. temperature curves were measured at 260 nm using a Gilford 260 spectrophotometer interfaced to an IBM PC computer and a Gilford Response II spectrophotometer. The buffer contained 100 mM Na$^+$, 10 mM phosphate and 0.1 mM EDTA, pH 7. Oligonucleotide concentration was 4 $\mu$M each strand determined from the absorbance at 85° C. and extinction coefficients calculated according to Puglisi and Tinoco, *Methods in Enzymol.* 1989, 180, 304–325. $T_m$ values, free energies of duplex formation and association constants were obtained from fits of data to a two state model with linear sloping baselines. Petersheim, M. and Turner, D. H., *Biochemistry* 1983, 22, 256–263. Reported parameters are averages of at least three experiments. For some oligonucleotides, free energies of duplex formation were also obtained from plots of $T_m^{-1}$ vs $\log_{10}$ (concentration). Borer, P. N., Dengler, B., Tinoco, I., Jr., and Uhlenbeck, O. C., *J. Mol. Biol.,* 1974, 86, 843–853.

EXAMPLE 9 ras Transactivation Reporter Gene System

The expression plasmid pSV2-oli, containing an activated (codon 12, GGC→GTC) H-ras cDNA insert under control of the constitutive SV40 promoter, was a gift from Dr. Bruno Tocque (Rhone-Poulenc Sante, Vitry, France). This plasmid was used as a template to construct, by PCR, a H-ras expression plasmid under regulation of the steroid-inducible mouse mammary tumor virus (MMTV) promoter. To obtain H-ras coding sequences, the 570 bp coding region of the H-ras gene was amplified by PCR. The PCR primers were designed with unique restriction endonuclease sites in their 5'-regions to facilitate cloning. The PCR product containing the coding region of the H-ras codon 12 mutant oncogene was gel purified, digested, and gel purified once again prior to cloning. This construction was completed by cloning the insert into the expression plasmid pMAMneo (Clontech Laboratories, California).

The ras-responsive reporter gene pRDO53 was used to detect ras expression. Owen et al., *Proc. Natl. Acad. Sci. U.S.A.* 1990, 87, 3866–3870.

EXAMPLE 10
Northern Blot Analysis of ras Expression in vivo

The human urinary bladder cancer cell line T24 was obtained from the American Type Culture Collection (Rockville Md.). Cells were grown in McCoy's 5A medium with L-glutamine (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of OptiMEM reduced-serum medium containing 2.5 µl DOTMA. Oligonucleotide was then added to the desired concentration. After 4 hours of treatment, the medium was replaced with McCoy's medium. Cells were harvested 48 hours after oligonucleotide treatment and RNA was isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, New York The human epithelioid carcinoma cell line HeLa 229 was obtained from the American Type Culture Collection (Bethesda, Md.). HeLa cells were maintained as monolayers on 6-well plates in Dulbecco's Modified Eagle's medium (DMEM) supplemented with 10% fetal bovine serum and 100 U/ml penicillin. Treatment with oligonucleotide and isolation of RNA were essentially as described above for T24 cells.

Northern hybridization: 10 µg of each RNA was electrophoresed on a 1.2% agarose/formaldehyde gel and transferred overnight to GeneBind 45 nylon membrane (Pharmacia LKB, Piscataway, N.J.) using standard methods. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, New York RNA was UV-crosslinked to the membrane. Double-stranded $^{32}$P-labeled probes were synthesized using the Prime a Gene labeling kit (Promega, Madison Wis.). The ras probe was a SalI-NheI fragment of a cDNA clone of the activated (mutant) H-ras mRNA having a GGC-to-GTC mutation at codon-12. The control probe was G3PDH. Blots were prehybridized for 15 minutes at 68° C. with the QuickHyb hybridization solution (Stratagene, La Jolla, Calif.). The heat-denatured radioactive probe (2.5×10$^6$ counts/2 ml hybridization solution) mixed with 100 µl of 10 mg/ml salmon sperm DNA was added and the membrane was hybridized for 1 hour at 68° C. The blots were washed twice for 15 minutes at room temperature in 2×SSC/0.1% SDS and once for 30 minutes at 60° C. with 0.1×SSC/0.1% SDS. Blots were autoradiographed and the intensity of signal was quantitated using an ImageQuant PhosphorImager (Molecular Dynamics, Sunnyvale, Calif.). Northern blots were first hybridized with the ras probe, then stripped by boiling for 15 minutes in 0.1×SSC/0.1% SDS and rehybridized with the control G3PDH probe to check for correct sample loading.

EXAMPLE 11
Antisense Oligonucleotide Inhibition of Proliferation of Cancer Cells Cells were cultured and treated with oligonucleotide essentially as described in Example 10. Cells were seeded on 60 mm plates and were treated with oligonucleotide in the presence of DOTMA when they reached 70% confluency. Time course experiment: On day 1, cells were treated with a single dose of oligonucleotide at a final concentration of 100 nM. The growth medium was changed once on day 3 and cells were counted every day for 5 days, using a counting chamber. Dose-response experiment: Various concentrations of oligonucleotide (10, 25, 50, 100 or 250 nM) were added to the cells and cells were harvested and counted 3 days later. Oligonucleotides 2570, 3985 and 4690 were tested for effects on T24 cancer cell proliferation.

EXAMPLE 12
Inhibition of PKC-α mRNA Expression by Chimeric (deoxy gapped) 2'-O-methyl oligonucleotides Oligonucleotides having SEQ. ID NO: 4 were synthesized as uniformly phosphorothioate chimeric oligonucleotides having a centered deoxy gap of varying lengths flanked by 2'-O-methylated regions. These oligonucleotides (500 nM concentration) were tested for effects on PKC-α mRNA levels by Northern blot analysis. Deoxy gaps of eight nucleotides or more gave maximal reduction of PKC-α mRNA levels (both transcripts) in all cases. These oligonucleotides reduced PKC-α mRNA by approximately 83% with a deoxy gap length of four nucleotides, and gave nearly complete reduction of PKC-α mRNA with a deoxy gap length of six or more.

The 2'-O-methyl chimeric oligonucleotides with four- or six-nucleotide deoxy gaps have an IC$_{50}$ for PKC-α mRNA reduction (concentration of oligonucleotide needed to give a 50% reduction in PKC-α mRNA levels) of 200–250 nM, as did the full-deoxy oligonucleotide (all are phosphorothioates throughout). The 2'-O-methyl chimeric oligonucleotide with an 8-nucleotide deoxy gap had an IC$_{50}$ of approximately 85 nM.

Several variations of this chimeric oligonucleotide (SEQ. ID NO: 4) were compared for ability to lower PKC-α mRNA levels. These oligonucleotides are shown in Table 5.

TABLE 5

Chimeric 2'-O-methyl/deoxy P = S oligonucleotides
bold = 2'-O-methyl; s = P = S linkage,
o = P = O linkage

| OLIGO | SEQUENCE | SEQ ID NO. |
|---|---|---|
| 3522 | AsAsAsAsCsGsTsCsAsGsCsCsAsTsGsGsTsCsCsC | 4 |
| 5352 | AsAsAsAsCsGsTsCsAsGsCsCsAsTsGsGsTsCsCsC | 4 |
| 6996 | AoAoAoAoCoGsTsCsAsGsCsCsAsTsGoGoToCoCoC | 4 |
| 7008 | AsAoAoAoCoGsTsCsAsGsCsCsAsTsGoGoToCoCsC | 4 |
| 7024 | AsAoAoAoCoGsToCsAoGsCoCsAsTsGoGoToCoCsC | 4 |

Figure 3:
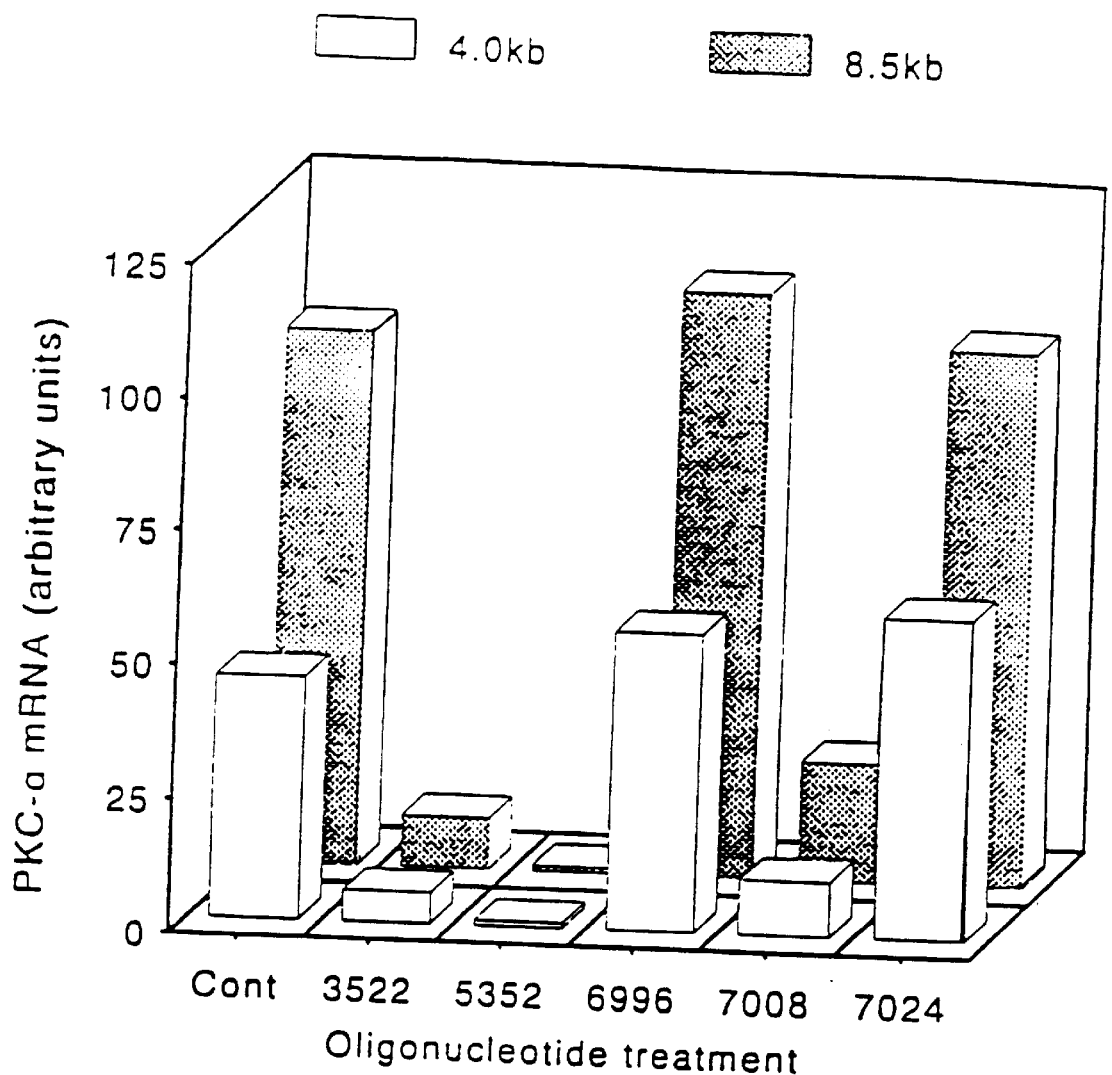
FIG. 3 is a bar graph showing the effects of several 2'-O-methyl chimeric oligonucleotides on PKC-α mRNA levels. Hatched bars represent the 8.5 kb transcript, and plain bars represent the 4.0 kb transcript.

Effect of these oligonucleotides on PKC-α mRNA levels is shown in FIG. 3. Oligonucleotides 7008, 3522 and 5352 show reduction of PKC-α mRNA, with 5352 being most active.

A series of 2'-O-propyl chimeric oligonucleotides was synthesized having SEQ ID NO: 4. These oligonucleotides are shown in Table 6.

TABLE 6

Chimeric 2'-O-propyl/deoxy P = S oligonucleotides
bold = 2'-O-propyl; s = P = S linkage,
o = P = O linkage

| OLIGO | SEQUENCE | SEQ ID NO. |
|---|---|---|
| 7199 | AsAsAsAsCsGsTsCsAsGsCsCsAsTsGsGsTsCsC | 4 |
| 7273 | AoAoAoAoCoGsTsCsAsGsCsCsAsTsGoGoToCoCoC | 4 |
| 7294 | AsAoAoAoCoGsTsCsAsGsCsCsAsTsGoGoToCoCsC | 4 |
| 7295 | AsAoAoAoCoGsToCsAoGsCoCsAsTsGoGoToCoCsC | 4 |

Figure 4:
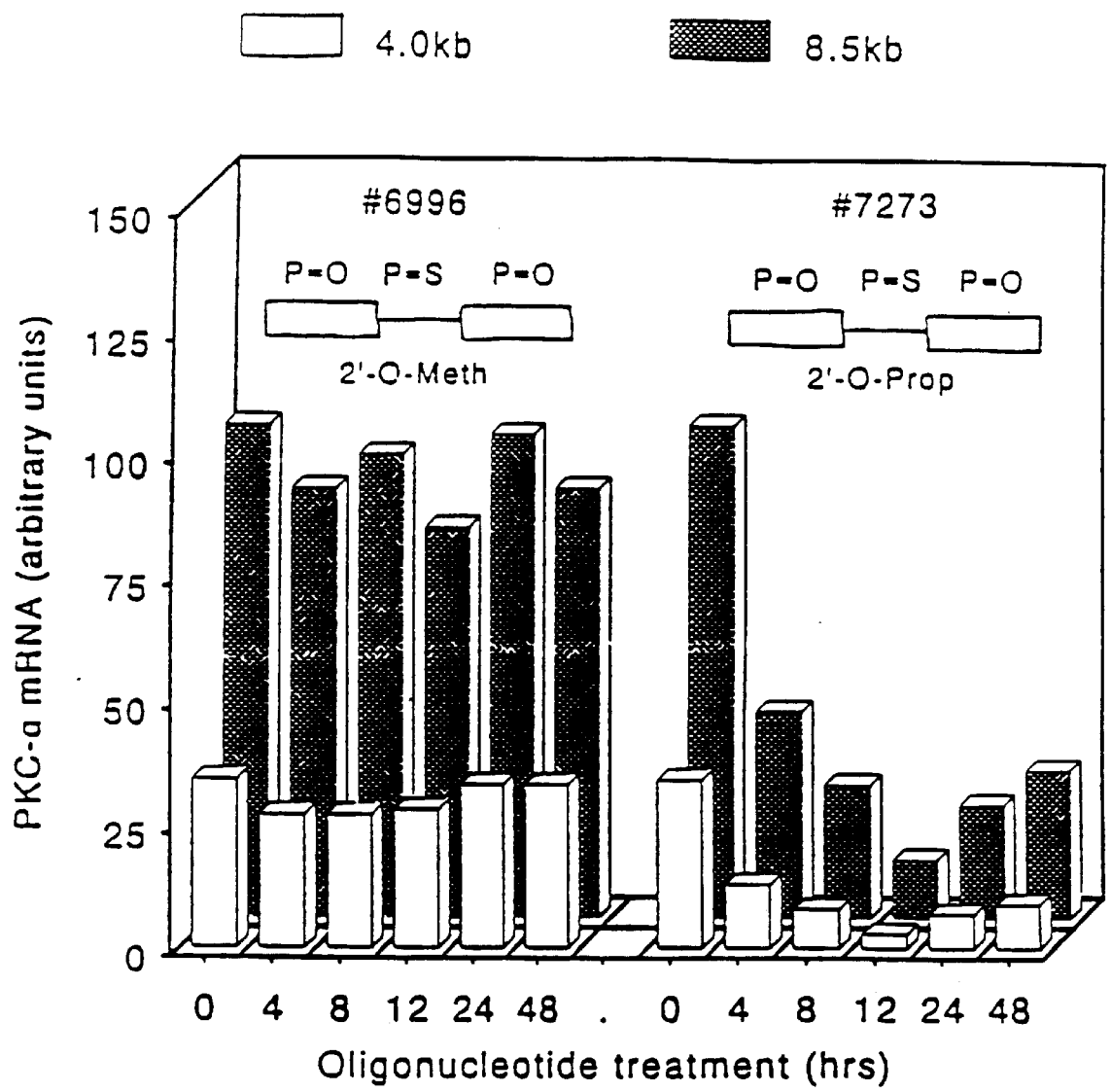
FIG. 4 is a bar graph showing the effects of several 2'-O-methyl and 2'-O-propyl chimeric oligonucleotides on PKC-α mRNA levels. Hatched bars represent the 8.5 kb transcript, and plain bars represent the 4.0 kb transcript.
Figure 5:
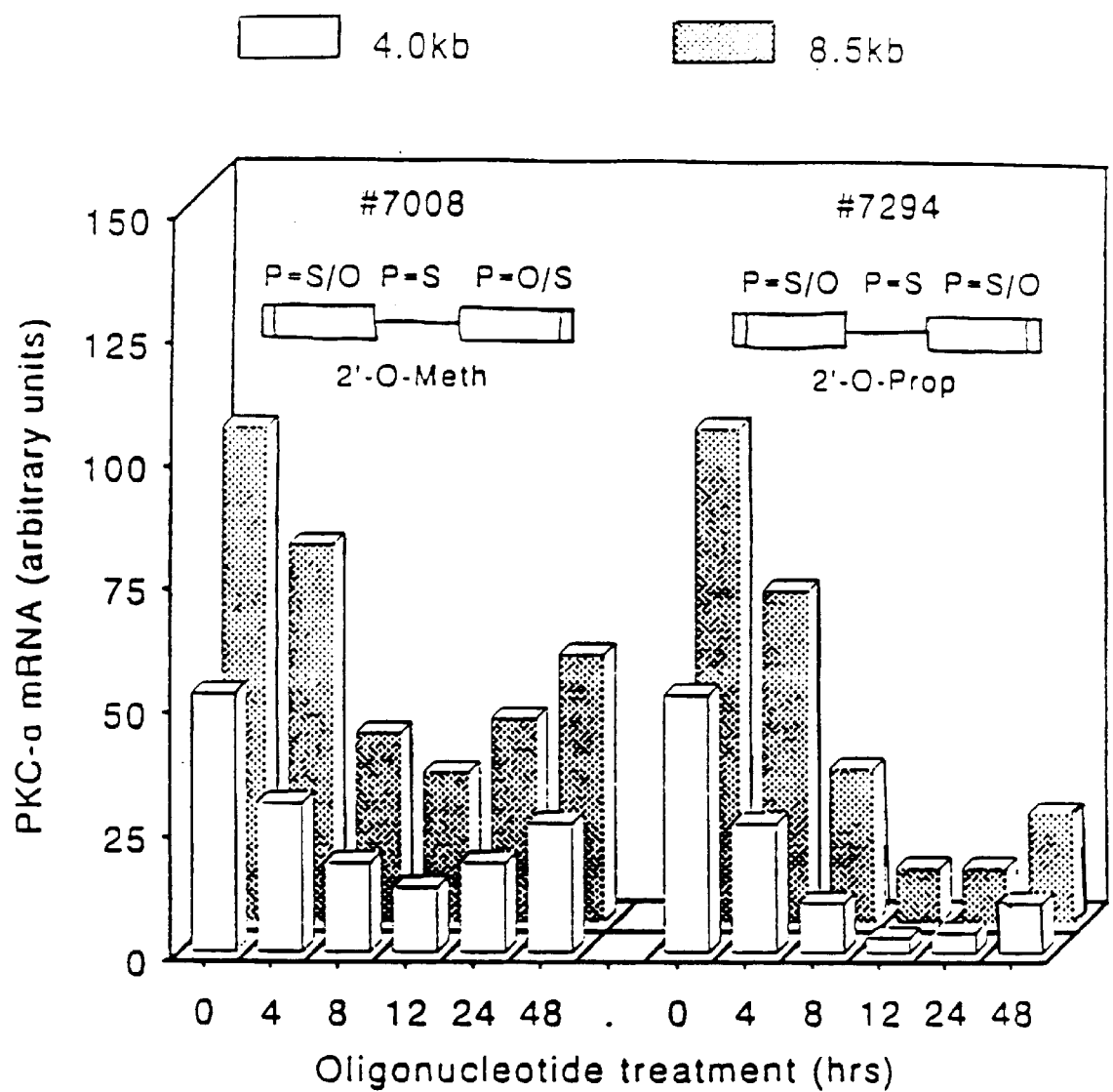
FIG. 5 is a bar graph showing the effects of additional 2'-O-methyl and 2'-O-propyl chimeric oligonucleotides on PKC-α mRNA levels. Hatched bars represent the 8.5 kb transcript, and plain bars represent the 4.0 kb transcript.

These 2'-O-propyl chimeric oligonucleotides were compared to the 2'-O-methyl chimeric oligonucleotides. Oligonucleotides 7273 and 7294 were more active than their 2'-O-methyl counterparts at lowering PKC-α mRNA levels. This is shown in FIGS. 4 and 5.

EXAMPLE 13
Additional Oligonucleotides Which Decrease PKC-α mRNA Expression

Additional phosphorothioate oligonucleotides targeted to the human PKC-α 3' untranslated region were designed and synthesized. These sequences are shown in Table 7.

TABLE 7

Chimeric 2'-O-propyl/deoxy P = S oligonucleotides
targeted to PKC-α 3'-UTR bold = 2'-O-propyl;
s = P = S linkage, o = P = O linkage

| OLIGO | SEQUENCE | SEQ ID NO. |
|---|---|---|
| 6632 | TsTsCs TsCsGs CsTsGs GsTsGs AsGsTs TsTsC | 5 |
| 6653 | TsTsCs TsCsGs CsTsGs GsTsGs AsGsTs TsTsC | 5 |
| 6665 | ToToCo TsCsGs CsTsGs GsTsGs AsGsTo ToToC | 5 |
| 7082 | TsCsTs CsGsCs TsGsGs TsGsAs GsTsTs TsC | 6 |
| 7083 | TsCsTs CsGsCs TsGsGs TsGsAs GsTsTs TsC | 6 |
| 7084 | ToCoTo CsGsCs TsGsGs TsGsAs GsToTo ToC | 6 |

Oligonucleotides 6632, 6653, 7082 and 7083 are most active in reducing PKC-α mRNA levels.

EXAMPLE 14
Inhibition of c-raf Expression by Chimeric Oligonucleotides

Chimeric oligonucleotides having SEQ ID NO. 7 were designed using the Genbank c-raf sequence HUMRAFR (Genbank listing x03484), synthesized and tested for inhibition of c-raf mRNA expression in T24 bladder carcinoma cells using a Northern blot assay. These chimeric oligonucleotides have central "gap" regions of 6, 8 or 10 deoxynucleotides flanked by two regions of 2'-O-methyl modified nucleotides, and are shown in Table 8. Backbones were uniformly phosphorothioate. In a Northern blot analysis, as described in Example 15, all three of these oligonucleotides (ISIS 6720, 6-deoxy gap; ISIS 6717, 8-deoxy gap; ISIS 6729, 10-deoxy gap) showed greater than 70% inhibition of c-raf mRNA expression in T24 cells. These oligonucleotides are preferred. The 8-deoxy gap compound (6717) showed greater than 90% inhibition and is more preferred.

TABLE 8

Chimeric 2'-O-methyl P = S deoxy "gap"
oligonucleotides bold = 2'-O-methyl

| OLIGO | SEQUENCE | Target site | SEQ ID NO. |
|---|---|---|---|
| 6720 | TCCCGCCTGTGACATGCATT | 3'UTR | 7 |
| 6717 | TCCCGCCTGTGACATGCATT | 3'UTR | 7 |
| 6729 | TCCCGCCTGTGACATGCATT | 3'UTR | 7 |

Additional chimeric oligonucleotides were synthesized having one or more regions of 2'-O-methyl modification and uniform phosphorothioate backbones. These are shown in Table 9. All are phosphorothioates; bold regions indicate 2'-O-methyl modified regions.

TABLE 9

Chimeric 2'-O-methyl P = S c-raf oligonucleotides

| OLIGO | SEQUENCE | Target site | SEQ ID NO. |
|---|---|---|---|
| 7848 | TCCTCCTCCCCGCGGCGGGT | 5'UTR | 8 |
| 7852 | TCCTCCTCCCCGCGGCGGGT | 5'UTR | 8 |
| 7849 | CTCGCCCGCTCCTCCTCCCC | 5'UTR | 9 |
| 7851 | CTCGCCCGCTCCTCCTCCCC | 5'UTR | 9 |
| 7856 | TTCTCGCCCGCTCCTCCTCC | 5'UTR | 10 |
| 7855 | TTCTCGCCCGCTCCTCCTCC | 5'UTR | 10 |
| 7854 | TTCTCCTCCTCCCCTGGCAG | 3'UTR | 11 |
| 7847 | CTGGCTTCTCCTCCTCCCCT | 3'UTR | 12 |
| 7850 | CTGGCTTCTCCTCCTCCCCT | 3'UTR | 12 |
| 7853 | CCTGCTGGTTCTCCTCCTC | 3'UTR | 13 |
| 9355 | CGGGAGGCGGTCACATTCGG | 5'UTR | 19 |

When tested for their ability to inhibit c-raf mRNA by Northern blot analysis, ISIS 7848, 7849, 7851, 7856, 7855, 7854, 7847, and 7853 gave better than 70% inhibition and are therefore preferred. Of these, 7851, 7855, 7847 and 7853 gave greater than 90% inhibition and are more preferred.

Additional chimeric oligonucleotides with various 2' modifications were prepared and tested. These are shown in Table 10. All are phosphorothioates; bold regions indicate 2'-modified regions.

TABLE 10

Chimeric 2'-modified P = S c-raf oligonucleotides

| OLIGO | SEQUENCE | TARGET SITE | MODIFIC. | SEQ ID NO. |
|---|---|---|---|---|
| 6720 | TCCCGCCTGTGACATGCATT | 3'UTR | 2'-O-Me | 7 |
| 6717 | TCCCGCCTGTGACATGCATT | 3'UTR | 2'-O-Me | 7 |
| 6729 | TCCCGCCTGTGACATGCATT | 3'UTR | 2'-O-Me | 7 |
| 8097 | TCTGGCGCTGCACCACTCTC | 3'UTR | 2'-O-Me | 14 |
| 9270 | TCCCGCCTGTGACATGCATT | 3'UTR | 2'-O-Pr | 7 |

TABLE 10-continued

Chimeric 2'-modified P = S c-raf oligonucleotides

| OLIGO | SEQUENCE | TARGET SITE | MODIFIC. | SEQ ID NO. |
|-------|----------|-------------|----------|------------|
| 9058 | TCCCGCCTGTGACATGCATT | 3'UTR | 2'-F | 7 |
| 9057 | TCTGGCGCTGCACCACTCTC | 3'UTR | 2'-F | 14 |

Of these, oligonucleotides 6720, 6717, 6729, 9720 and 9058 are preferred. Oligonucleotides 6717, 6729, 9720 and 9058 are more preferred.

EXAMPLE 15
Northern Blot Analysis of Inhibition of c-raf mRNA Expression

The human urinary bladder cancer cell line T24 was obtained from the American Type Culture Collection (Rockville Md.). Cells were grown in McCoy's 5A medium with L-glutamine (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of OptiMEM reduced-serum medium containing 2.5 µl DOTMA. Oligonucleotide with lipofectin was then added to the desired concentration. After 4 hours of treatment, the medium was replaced with McCoy's medium. Cells were harvested 24 to 72 hours after oligonucleotide treatment and RNA was isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, New York. Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene, La Jolla, Calif.) and hybridized to random-primed $^{32}$P-labeled c-raf cDNA probe (obtained from ATCC) or G3PDH probe as a control. RNA was quantitated using a Phosphorimager (Molecular Dynamics, Sunnyvale, Calif.).

EXAMPLE 16
Oligonucleotide Inhibition of Rev Gene Expression

The chimeric oligonucleotides used in this assay are shown in Table 11 below.

TABLE 11

Chimeric 2'-O-propyl/deoxy P = S oligonucleotides targeted to HIV rev gene bold = 2'-O-propyl; s = P = S linkage; o = P = O linkage

| OLI-GO | SEQUENCE | SEQ. ID NO. |
|--------|----------|-------------|
| 8907 | UoAoGoGoAoGoAsUsGsCsCsUsAsAoGoGoCoUoUoU | 20 |
| 8908 | GoCoUoAoUoGoUsCsGsAsCsAsCsCoCoAoAoUoUoC | 21 |
| 8909 | CoAoUoAoGoGoAsGsAsUsGsCsCsUoAoAoGoGoCoT | 22 |

Transfection and Luciferase assay: 3T3 cells were maintained in DMEM with glucose, L-glutamine, sodium pyruvate and 10% fetal bovine serum (GIBCO). For all experiments, cells were seeded the previous night at 75,000 cells/well in 6-well plates (Falcon). Transfections were performed using the standard CaPO$_4$ method. For each set of replicates, 15 µg/mL of pSG5/rev plasmid, 18 µg/mL pHIVenu-luc and 2 µg/mL of Rep 6 were precipitated and 200 µL of this was dripped on each well. The precipitate was allowed to incubate on cells for 7 hours at 37° C. The media was then aspirated, the cells washed once with PBS, and fresh complete media added for overnight incubation. Following incubation, the media was removed, cells washed with 2 mL of OPTIMEM (GIBCO) and 1 mL of OPTIMEM containing 2.5 µg/mL of Lipofectin (GIBCO-BRL) and the oligonucleotide added. The mixture was incubated for 4 hours at 37° C., at which point it was aspirated off the cells and complete media was added. Two hours after this treatment, 0.2 µg/mL of dexamethasone (Sigma) was added to all wells to allow induction of the MMTV promoter of pHIVenu-luc.

The Luciferase assay was performed 24 hours later, as follows: The wells were washed twice with PBS and the cells were harvested by scraping in 200 µL of lysis buffer (1% Triton, 25 mM glycylglycine, pH 7.8, 15 mM MgSO$_4$, 4 mM EGTA and 1 mM DTT)> The lysate was clarified by microfuging for 5 minutes at 11,500 rpm in the cold. 100 µL of the lysate was then combined in a microtiter plate with 50 µL of assay buffer (25 mM glycylglycine, pH 7.8, 15 mM MgSO$_4$, 4 mM EGTA, 15 mM potassium phosphate, pH 7.8, 1 mM DTT and 7.5 mM ATP). Luc detection was performed using a microtiter luminescent reader (Dynatech Laboratories). The reactions were started by injecting 50 µL of 1× luciferase solution (Sigma). The 1× solution was diluted in luciferin buffer (25 mM glycylglycine, pH 7.8, 15 mM MgSO$_4$, 4 mM EGTA and 4 mM DTT) prior to use from a 10× stock (10 mM luciferin in 10 mM DTT). Samples were counted for 20 seconds. The kinetics of firefly luc light emission are characterized by a flash period lasting a few seconds followed by a period of lower light intensity emission lasting several minutes.

Rev and RRE RNA synthesis: pSG5-Rev contains the Rev gene adjacent to a T7 promoter. BglII linearized pSG5-Rev was used as a DNA template for transcription with T7 RNA polymerase. A template for the production of RRE RNA was produced by PCR. For RNA synthesis, DNA templates were used at 0.2 to 1.0 mg/mL, with 5 mM each of ATP, CTP and GTP, 0.5 mM of UTP, 10 mM of DTT, 40 mM of Tris-HCl, pH 7.5, 6 mM of MgCl$_{2,4}$ mM of Spermidine, 500 U/mL of RNAsin at 20 U/µL, 2500 µCi/mL of α $^{32}$p UTP at 10 mCi/mL and 1000 U/mL of T7 RNA polymerase. The reaction was incubated for 1 hour at 37° C. The transcription reaction was terminated by adding formamide loading buffer and was run in a denaturing polyacrylamide gel containing 8 M urea. The RNA was eluted from the gel according to the procedure of Schwartz et al. (*Gene*, 1990, 88, 197).

EXAMPLE 17
Immunoassay for Antiviral Screening

NHDF cells were seeded in 96-well culture plates at a density of 15,000 cells/well in serum-free FGM. Established monolayers were pretreated with the oligonucleotide overnight in FGM prior to infection. After pretreatment, cells were rinsed thrice with fresh, prewarmed FGM, and virus in 100 µL of FGM/well was added to achieve an MOI of 0.05

PFU/cell. After 2 hours of incubation at 37° C., virus was removed and fresh medium (100 μL/well) containing the oligonucleotide was added. Medium was exchanged 2 days after infection with fresh medium containing the oligonucleotide, and 6 days after infection, the cells were fixed in absolute ethanol and dried in preparation for antibody staining. A modified protocol was used for some assays in which FGM was supplemented with low levels of FBS (0.2%), and the incubation period after infection was shortened from 6 days to 3 days. The shorter assay eliminated the need to exchange medium 2 days after infection. Both assays yielded comparable values for 50% effective concentrations (EC50s).

Fixed cells were blocked in a solution of PBS containing 2% bovine serum albumin (BSA), and mouse monoclonal antibody (1H10, supplied by Eisai Co., Ltd., Japan) was added in a 1:2000 dilution in PBS-1% BSA. The 1H10 antibody recognizes an abundant late HCMV polypeptide approximately 65 kDa in size. Detection of bound monoclonal antibody was facilitated with biotinylated goat anti-mouse immunoglobulin G abd streptavidin-coupled β-galactosidase (GIBCO-BRL, Gaithersburg, Md.). Chlorophenol red β-D-galactopyranoside was used as a substrate for β-galactosidase, and activity was determined by measuring the optical density at 575 nm of individual wells with a BioTex model EL312e microplate reader.

The oligonucleotides used in this assay are shown in Table 12 below.

TABLE 12

Inhibition of CMV replication by chimeric
2'-O-methyl P = S oligonucleotides
bold = 2'-O-methyl

| OLIGO | SEQUENCE | SEQ. ID NO. |
|---|---|---|
| 4325 | GCG UUT GCT CTT CTT CUU GCG | 23 |
| 4326 | GCG UUU GCT CTT CTU CUU GCG | 24 |

EXAMPLE 18

Evaluation of Oligonucleotides 270 and 330 in an HCV H8Ad17 Protein Assay

A Western blot assay employing affinity-purified human polyclonal anti-HCV serum and $^{125}$I-conjugated goat anti-human IgG was developed in place of ELISA assays previously used to evaluate effects of oligonucleotides on HCV core protein levels. Six-well plates were seeded with H8 cells at $3.5 \times 10^5$ cells/well. Cells were grown overnight. Cells were treated with oligonucleotide in Optimem containing 5 μg/mL lipofectin for 4 hours. Cells were fed with 2 mL H8 medium and allowed to recover overnight. To harvest cells, cells were washed once with 2 mL PBS, lysed in 100 μL Laemmli buffer and harvested by scraping. For electrophoresis, cell lysates were boiled, and 10–14 μL of cell lysate was loaded on each lane of a 16% polyacrylamide gel. After electrophoresing, proteins were transferred electrophoretically onto PVDF membrane. The membrane was blocked in PBS containing 2% goat serum and 0.3% Tween-20, and incubated overnight with primary antibody (human anti-core antibody 2243 and rabbit anti-G3PDH antibody). The membrane was washed 5x5 minutes in buffer, then incubated with secondary antibodies for 4–8 hours ($^{125}$I-conjugated goat anti-human, and $^{125}$I-conjugated goat anti-rabbit). The membrane was washed 5x5 minutes in buffer, sealed in plastic and exposed in a PhosphorImager cassette overnight. Bands were quantitated on the PhosphorImager (Molecular Dynamics, Sunnyvale Calif.), normalized to G3PDH expression levels, and results were plotted as a percentage of control untreated cells.

The oligonucleotides evaluated by this Western blot assay are shown in Table 13. In the sequences shown, capital letters represent base sequence, small letters (o or s) represent internucleoside linkage, either phosphodiester (P=O) or phosphorothioate (P=S), respectively. Bold=2'-fluoro. *=2'-O-butylimidazole. +=2'-O-propylamine.

TABLE 13

| Oligo # | Sequence | SEQ. ID NO. |
|---|---|---|
| 270A | GsTsAsCsCsAsCsAsAsAsGsGsCsCsTsTsTsCsGsCsG | 25 |
| 270B | GsTsAsCsCsAsCsAsAsAsGsGsCsCsTsTsTsCsGsCsG | 25 |
| 270C | Go*To*AoCoCoAoCoAoAoGoGoCoCoTo*ToTo*CoGoCoG | 25 |
| 270D | Go⁺To⁺AoCoCoAoCoAoAoGoGoCoCoTo⁺To⁺ToCoGoCoG | 25 |
| 330A | GsTsGsCsTsCsAsTsGsGsTsGsCsAsCsGsGsTsCsT | 26 |
| 330B | GsTsGsCsTsCsAsTsGsGsTsGsCsAsCsGsGsTsCsT | 26 |
| 330C | Go*To*GoCoToCoAoToGoGoToGoCoAo*CoGo*GoToCoT | 26 |
| 330D | Go⁺To⁺GoCoToCoAoToGoGoToGoCoAo⁺Co⁺GoGoToCoT | 26 |

EXAMPLE 19

Synthesis of 2,6-Diamino-9-(2-O-octadecyl-β-D-ribofuranosyl)purine 2,6-Diamino-9-(β-D-ribofuranosyl)purine (50 g, 180 mmol) and sodium hydride (7 g) in DMF (1 L) were heated to boiling for 2 hr. Iodooctadecane (100 g) was added at 150° C. and the reaction mixture allowed to cool to RT. The reaction mixture was stirred for 11 days at RT. The solvent was evaporated and the residue purified by silica gel chromatography. The product was eluted with 5% MeOH/CH$_2$Cl$_2$. The appropriate fractions were evaporated to yield the product (11 g). $^1$H NMR (DMSO-d$_6$) δ 0.84 (t, 3, CH$_2$); 1.22 (m, 32, O—CH$_2$—CH$_2$—(CH$_2$)$_{16}$); 1.86 (m, 2, O—CH$_2$CH$_2$); 3.25 (m, 2, O—CH$_2$); 3.93 (d, 1, 4'H), 4.25 (m, 1, 3'H); 4.38 (t, 1, 2'H); 5.08 (d, 1, 3'-OH); 5.48 (t, 1, 5'-OH); 5.75 (s, 2, 6-NH$_2$); 5.84 (d, 1, 1'-H); 6.8 (s, 2, 2-NH2); and 7.95 (s, 1, 8-H)

EXAMPLE 20

Synthesis of 2'-O-Octadecylguanosine 2,6-Diamino-9-(2-O-octadecyl-β-D-ribofuranosyl) purine (10 g) in 0.1 M sodium phosphate buffer (50 ml, pH 7.4), 0.1 M tris buffer (1000 ml, pH 7.4) and DMSO (1000 ml) was treated with adenosine deaminase (1.5 g) at RT. At day 3, day 5 and day 7 an additional aliquot (500 mg, 880 mg and 200 mg, respectively) of adenosine deaminase was added. The reaction was stirred for a total of 9 day and purification by silica gel chromatography yielded the product (2 g). An analytical sample was recrystallized from MeOH $^1$H NMR (DMSO-d$_6$) δ 0.84 (t, 3, CH$_3$), 1.22 [s, 32, O—CH$_2$—CH$_2$—(CH$_2$)$_{16}$], 5.07 (m, 2, 3'-OH and 5'-OH); 5.78 (d, 1, 1'-H); 6.43 (s, 2, NH$_2$), 7.97 (s, 1, 8-H) and 10.64 (s, 1, NH$_2$). Anal. Calcd. for C$_{28}$H$_{49}$N$_5$O$_5$: C, 62.80; H, 9.16; N, 12.95. Found: C, 62.54; H, 9.18; N, 12.95.

EXAMPLE 21
Synthesis of $N^2$-Isobutyryl-2'-O-Octadecylguanosine

2'-O-Octadecylguanosine (1.9 g) in pyridine (150 ml) was cooled in an ice bath, and treated with trimethylsilyl chloride (2 g, 5 eq) and isobutyryl chloride (2 g, 5 eq). The reaction mixture was stirred for 4 hours, during which time it was allowed to warm to room temperature. The solution was cooled, water added (10 mL) and stirred for an additional 30 minutes. Concentrated ammonium hydroxide (10 mL) was added and the solution concentrated in vacuo. The residue was purified by silica gel chromatography (eluted with 3% MeOH/EtOAc) to yield 1.2 g of product. $^1$H NMR (DMSO-$d_6$) δ 0.85 (t, 3, $CH_3$), 1.15 (m, 38, O—$CH_2CH_2(CH_2)_{16}$, $CH(CH_3)_2$), 2.77 (m, 1, $CH(CH_3)_2$), 4.25 (m, 2, 2'-H and 3'-H); 5.08 (t, 1, 5'-OH), 5.12 (d, 1, 3'-OH), 5.87 (d, 1, 1'-H), 8.27 (s, 1, 8-H), 11.68 (s, 1, $NH_2$) and 12.08 (s, 1, $NH_2$). Anal. Calcd. for $C_{32}H_{55}N_5O_6$: C, 63.47; H, 9.09; N, 11.57. Found: C, 63.53; H, 9.20; N, 11.52. Prior to incorporating this product into an oligonucleotide, it was converted to $N^2$-Isobutyryl-5'-dimethoxytrityl-2'-O-octadecylguanosine and then to a phosphoramidite according to the procedures described in International Publication Number WO 94/02501, published Feb. 3, 1994.

EXAMPLE 22
Diagnostic Assay for the Detection of mRNA Overexpression

Oligonucleotides are radiolabeled after synthesis by $^{32}$P labeling at the 5' end with polynucleotide kinase. Sambrook et al. ["*Molecular Cloning. A Laboratory Manual*," Cold Spring Harbor Laboratory Press, 1989, Volume 2, pg. 11.31–11.32]. Radiolabeled oligonucleotide is contacted with tissue or cell samples suspected of mRNA overexpression, such as a sample from a patient, under conditions in which specific hybridization can occur, and the sample is washed to remove unbound oligonucleotide. A similar control is maintained wherein the radiolabeled oligonucleotide is contacted with normal cell or tissue sample under conditions that allow specific hybridization, and the sample is washed to remove unbound oligonucleotide. Radioactivity remaining in the sample indicates bound oligonucleotide and is quantitated using a scintillation counter or other routine means. Comparison of the radioactivity remaining in the samples from normal and diseased cells indicates overexpression of the mRNA of interest.

Radiolabeled oligonucleotides of the invention are also useful in autoradiography. Tissue sections are treated with radiolabeled oligonucleotide and washed as described above, then exposed to photographic emulsion according to standard autoradiography procedures. A control with normal cell or tissue sample is also maintained. The emulsion, when developed, yields an image of silver grains over the regions overexpressing the mRNA, which is quantitated. The extent of mRNA overexpression is determined by comparison of the silver grains observed with normal and diseased cells.

Analogous assays for fluorescent detection of mRNA expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described for radiolabeled oligonucleotides except that instead of a scintillation counter, a fluorescence microscope is used to detect the fluorescence. Comparison of the fluorescence observed in samples from normal and diseased cells enables detection of mRNA overexpression.

EXAMPLE 23
Detection of Abnormal mRNA Expression

Tissue or cell samples suspected of expressing abnormal mRNA are incubated with a first $^{32}$P or fluorescein-labeled oligonucleotide which is targeted to the wild-type (normal) mRNA. An identical sample of cells or tissues is incubated with a second labeled oligonucleotide which is targeted to the abnormal mRNA, under conditions in which specific hybridization can occur, and the sample is washed to remove unbound oligonucleotide. Label remaining in the sample indicates bound oligonucleotide and can be quantitated using a scintillation counter, fluorimeter, or other routine means. The presence of abnormal mRNA is indicated if binding is observed in the case of the second but not the first sample.

Double labeling can also be used with the oligonucleotides and methods of the invention to specifically detect expression of abnormal mRNA. A single tissue sample is incubated with a first $^{32}$P-labeled oligonucleotide which is targeted to wild-type mRNA, and a second fluorescein-labeled oligonucleotide which is targeted to the abnormal mRNA, under conditions in which specific hybridization can occur. The sample is washed to remove unbound oligonucleotide and the labels are detected by scintillation counting and fluorimetry. The presence of abnormal mRNA is indicated if the sample does not bind the $^{32}$P-labeled oligonucleotide (i.e., is not radioactive) but does retain the fluorescent label (i.e., is fluorescent).

EXAMPLE 24
Plasma Uptake and Tissue Distribution of Oligonucleotides in Mice The following oligonucleotides were prepared:

UsGsCsAsTsCsCsCsCsCsAsGsGsCsCsAsCsCsAsT, SEQ ID NO. 27

UsGsCsAsTsCsCsCsCsAsGsGsCsCsAsCsCsAsT, SEQ ID NO. 27

UsGsCsAsTsCsCCCCAGGCsCsAsCsCsAsT, SEQ ID NO. 27 wherein bold type indicated a 2'-O-propyl substituent, "s" indicates a phosphorothioate linkage and the absence of "s" indicates a phosphodiester linkage in the respective oligonucleotides. The first oligonucleotide is identified as Isis 3082, the second as Isis 9045 and the third as Isis 9046 in the FIGS. 6, 7, 8 and 9. The oligonucleotides were tritiated as per the procedure of Graham et al., *Nuc. Acids Res.*, 1993, 16, 3737–3743.

Animals and Experimental Procedure

For each oligonucleotide studied, twenty male Balb/c mice (Charles River), weighing about 25 gm, were randomly assigned into one of four treatment groups. Following a one-week acclimation, mice received a single tail vein injection of $^3$H-radiolabeled oligonucleotide (approximately 750 nmoles/kg; ranging from 124–170 μCi/kg) administered in phosphate buffered saline, pH 7.0. The concentration of oligonucleotide in the dosing solution was approximately 60 μM. One retro-orbital bleed (at either 0.25, 0.5, 2, or 4 hours post-dose) and a terminal bleed (either 1, 3, 8 or 24 hours post-dose) was collected from each group. The terminal bleed was collected by cardiac puncture following ketamine/xylazine anesthesia. An aliquot of each blood sample was reserved for radioactivity determination and the remaining blood was transferred to an EDTA-coated collection tube and centrifuged to obtain plasma. Urine and feces were collected at intervals (0–4, 4–8 and 8–24 hours) from the group terminated at 24 hours.

At termination, the liver, kidneys, spleen, lungs, heart, brain, sample of skeletal muscle, portion of the small intestine, sample of skin, pancreas, bone (both femurs containing marrow) and two lymph nodes were collected from each mouse and weighed. Feces were weighed, then homogenized 1:1 with distilled water using a Brinkmann Polytron homogenizer (Westbury, N.Y.). Plasma, tissues, urine and feces homogenate were divided for the analysis of radioactivity by combustion and for determination of intact oligonucleotide content. All samples were immediately frozen on dry ice after collection and stored at −80° C. until analysis.

Analysis of Radioactivity in Plasma, Tissue, and Excreta

Plasma and urine samples were weighed directly into scintillation vials and analyzed directly by liquid scintillation counting after the addition of 15 ml of BetaBlend (ICN Biomedicals, Costa Mesa, Calif.). All other samples (tissues, blood and homogenized feces) were weighed into combustion boats and oxidized in a Biological Materials Oxidizer (Model OX-100; R. J. Harvey Instrument Corp., Hillsdale, N.J.). The $^3H_2O$ was collected in 20 ml of cocktail, composed of 15 ml of BetaBlend and 5 ml of Harvey Tritium Cocktail (R. J. Harvey Instrument Corp., Hillsdale, N.J.). The combustion efficiency was determined daily by combustion of samples spiked with a solution of $^3H$-mannitol and ranged between 73.9–88.3%. Liquid scintillation counting was performed using a Beckman LS 9800 or LS 6500 Liquid Scintillation System (Beckman Instruments, Fullerton, Calif.). Samples were counted for 10 minutes with automatic quench correction. Disintegration per minute values were corrected for the efficiency of the combustion process.

Analysis of Data

Radioactivity in samples was expressed as disintegrations per minute per gram of sample. These values were divided by the specific activity of the radiolabel to express the data in nanomole-equivalents of total oligonucleotide per gram of sample, then converted to percent of dose administered per organ or tissue. Assuming a tissue density of 1 gm/ml, the nmole/gram data were converted to a total $\mu M$ concentration. To calculate the concentration of intact oligonucleotide in plasma, liver or kidney at each time point, the mean total AM concentrations were divided by the percent of intact oligonucleotide in the dosing solution (82–97%), then multiplied by the mean percentage of intact oligonucleotide at each time point as determined by CGE or HPLC. This data was then used for the calculation of tissue half-lives by linear regression and to compare the plasma pharmacokinetics of the different modified oligonucleotides. The pharmacokinetic parameters were determined using PCNONLIN 4.0 (Statistical Consultants, Inc., Apex, N.C.). After examination of the data, a one-compartment bolus input, first order output model (library model 1) was selected for use.

Figure 6:
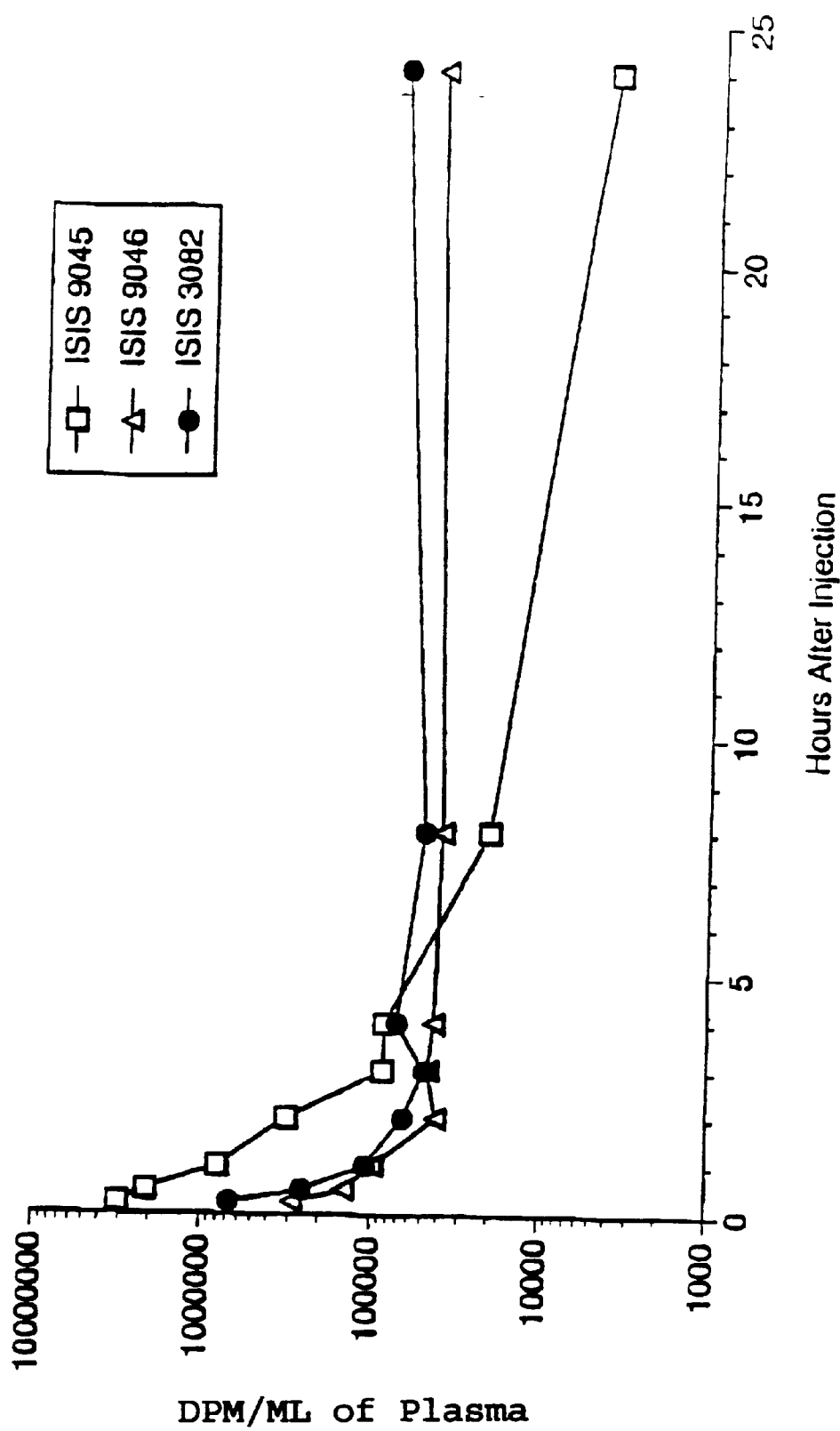
FIG. 6 is a graph showing mouse plasma concentrations of a control compound and two of the compounds of the invention. The plasma concentration is plotted verses time.
Figure 7:
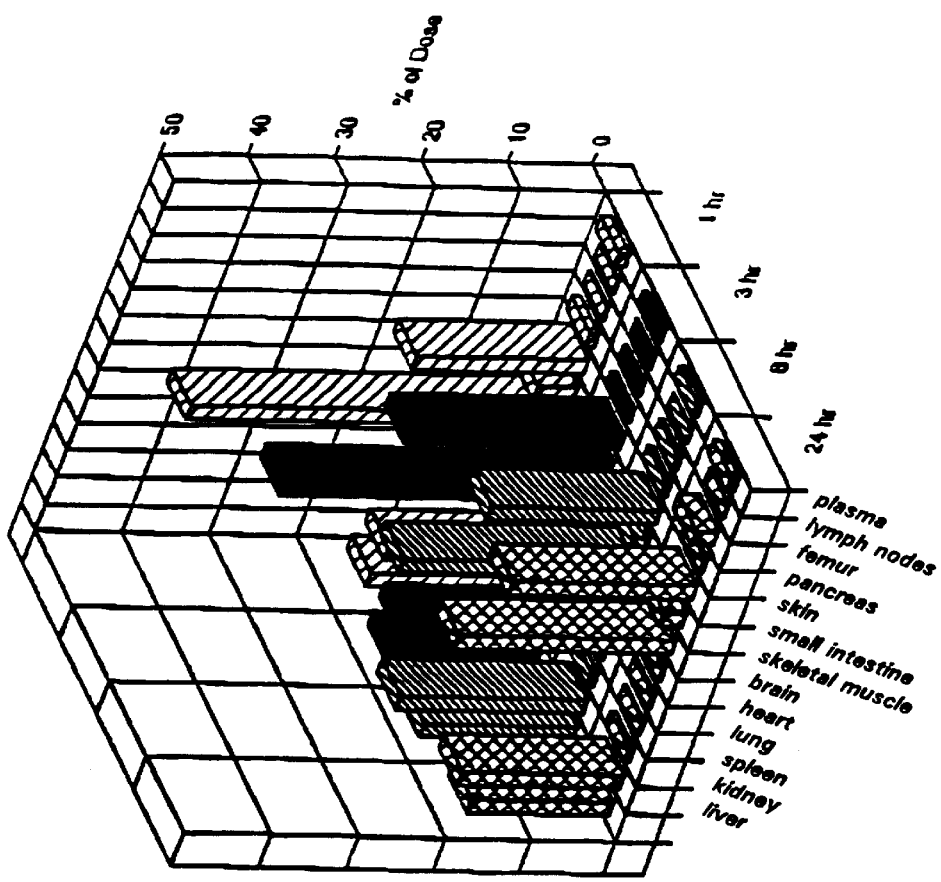
FIG. 7 is a three dimensional graph showing distribution of a control compound among various tissue in the mouse. Specific tissues are shown on one axis, time on a second axis and percent of dose on the third axis. The compound was delivered by intravenous injected.
Figure 8:
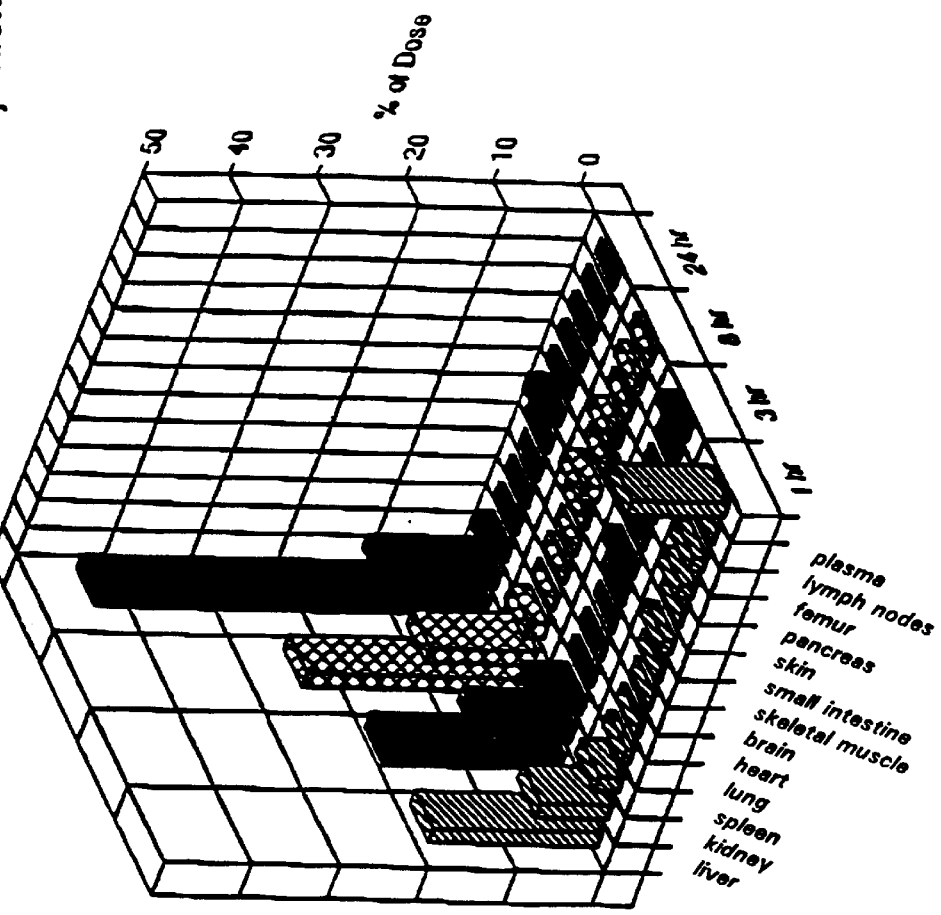
FIG. 8 is a three dimensional graph showing distribution of a compound of the invention among various tissue in the mouse. Specific tissues are shown on one axis, time on a second axis and percent of dose on the third axis.

The result of the animal plasma uptake and tissue distribution tests are illustrated graphically in FIGS. 6, 7, 8 and 9. As is seen in FIG. 6, plasma concentration of each of the test oligonucleotides decrease from the initial injection levels to lower levels over the twenty-four hour test period. Plasma concentrations of the oligonucleotides of the invention were maintained at levels equivalent to those of the non-conjugate bearing phosphorothioate. All of the test compounds were taken up from the plasma to tissues as is shown in FIGS. 7, 8 and 9. The compounds of the invention had different distribution between the various tissues. FIG. 7 shows the distribution pattern for the control oligonucleotide, identified as ISIS 3082, a phosphorothioate oligonucleotide. FIG. 8 shows the distribution pattern for a first compound of the invention, an oligonucleotide, identified as ISIS 9045, having a 2'-substituent at each nucleotide. FIG. 9 shows the distribution pattern for a further compound of the invention, a "gap mer" oligonucleotide, identified as ISIS 9046, having a 2'-substituent and phosphodiester linkages at each nucleotide at "flanking" sections of the oligonucleotide and 2'-deoxy, phosphorothioate nucleotides in a central or gap region.

---

What is claimed is:

1. An oligonucleotide comprising a sequence of nucleotide unite specifically hybridizable with DNA or RNA wherein said sequence is divided into a first segment and a second segment, wherein:

said first segment is adjacent said second segment and does not overlap said second segment;

said first segment has at least two consecutively located 2'-F nucleotide units;

said second segment is composed of at least five consecutively located nucleotide units having 2'-H sugar moieties; and said oligonucleotide hybridizes with said DNA or RNA with higher binding affinity than a corresponding oligomer in which said at least two consecutively located 2'-F nucleotide units are 2'-H nucleotide units.

2. The oligonucleotide of claim 1 wherein said nucleotide units of said first and second segments are connected by phosphodiester or phosphorothioate linkages.

3. The oligonucleotide of claim 2 wherein said nucleotide units of said first and second segments are connected by phosphodiester linkages.

4. The oligonucleotide of claim 2 wherein said nucleotide units of said first and second segments are connected by phosphorothioate linkages.

5. The oligonucleotide of claim 2 wherein said nucleotide units of said first segment are connected by phosphodiester linkages and said nucleotide units of said second segment are connected by phosphorothioate linkages.

6. The oligonucleotide of claim 2 wherein said nucleotide units of said first segment are connected by phosphorothioate linkages and said nucleotide units of said second segment are connected by phosphodiester linkages.

7. The oligonucleotide of claim 1 having 5 to 50 nucleotide units.

8. An oligonucleotide comprising a sequence of nucleotide units specifically hybridizable with DNA or RNA, wherein said sequence is divided into a first segment, a second segment, and a third segment wherein:

said first segment and said third segment each has at least two consecutively located 2'-deoxy-2'-fluoro nucleotide units; and said second segment is positioned adjacent to and between said first segment and said third segment and is composed of at least three consecutively located nucleotide units having 2'-deoxy sugar moieties.

9. The oligonucleotide of claim 8 wherein said nucleotide units of said first, second and third segments are connected by phosphodiester or phosphorothioate linkages.

10. The oligonucleotide of claim 9 wherein said nucleotide units of said first, second and third segments are connected by phosphodiester linkages.

11. The oligonucleotide of claim 9 wherein said nucleotide units of said first, second and third segments are connected by phosphorothioate linkages.

12. The oligonucleotide of claim 9 wherein said nucleotide units of said first and third segments are connected by phosphodiester linkages and said nucleotide units of said second segment are connected by phosphorothioate linkages.

13. The oligonucleotide of claim 9 wherein said nucleotide units of said first and third segments are connected by phosphorothioate linkages and said nucleotide units of said second segment are connected by phosphodiester linkages.

14. The oligonucleotide of claim 8 wherein said second segment has at least five nucleotide units.

15. The oligonucleotide of claim 8 having 5 to 50 nucleotide units.

* * * * *

(12) EX PARTE REEXAMINATION CERTIFICATE (8349th)
United States Patent
Cook et al.

(10) Number: US 5,955,589 C1
(45) Certificate Issued: Jun. 28, 2011

(54) GAPPED 2' MODIFIED OLIGONUCLEOTIDES

(75) Inventors: Phillip Dan Cook, Vista, CA (US); Brett P. Monia, Carlsbad, CA (US)

(73) Assignee: Isis Pharmaceuticals, Inc., Carlsbad, CA (US)

Reexamination Request:
No. 90/010,996, Jun. 24, 2010

Reexamination Certificate for:
Patent No.: 5,955,589
Issued: Sep. 21, 1999
Appl. No.: 08/465,880
Filed: Jun. 6, 1995

Related U.S. Application Data

(63) Continuation-in-part of application No. 08/244,993, filed as application No. PCT/US92/11339 on Dec. 23, 1992, now Pat. No. 5,623,065, which is a continuation-in-part of application No. 07/814,961, filed on Dec. 24, 1991, now abandoned.

(51) Int. Cl.

| | |
|---|---|
| A61K 31/00 | (2006.01) |
| A61K 31/70 | (2006.01) |
| A61K 31/7125 | (2006.01) |
| A61K 48/00 | (2006.01) |
| A61P 31/00 | (2006.01) |
| A61P 35/00 | (2006.01) |
| A61P 43/00 | (2006.01) |
| C07H 19/04 | (2006.01) |
| C07H 21/00 | (2006.01) |
| C07H 21/04 | (2006.01) |
| C07H 19/00 | (2006.01) |
| C07K 9/00 | (2006.01) |
| C07K 14/00 | (2006.01) |
| C12N 15/09 | (2006.01) |
| C12N 15/11 | (2006.01) |
| C12Q 1/68 | (2006.01) |

(52) U.S. Cl. .............. 536/23.1; 536/24.1; 536/24.2; 536/24.3; 536/24.31; 536/24.32; 536/25.2; 536/25.3

(58) Field of Classification Search .............. None
See application file for complete search history.

(56) References Cited

PUBLICATIONS

Shibahara et al., "Site–Directed Cleavage of RNA," Nucleic Acids Research (1987) 15:4403–4415.

Ikehara et al., "Polynucleotides. LVI. Synthesis and Properties of poly(d'deoxy–2'fluoroinosinic acid)," Nucleic Acids Research (1978) 5:3315–3324.

Quartin et al., "Number and Distribution of Methylphosphonate Linkages in Oligodeoxynucleotides Affect Exo– and ..." Nucleic Acids Research (1989) 17:7253–7262.

Uhlmann et al., "Antisense Oligonucleotides: A New Therapeutic Principle," Chemical Reviews (1990) 90:543–584.

Kakiuchi et al., "Polynucleotide Helix Geometry and Stability," Journal of Biological Chemistry (1982) 257(4):1924–1928.

Metelev et al., "Influence of Probe Structure on Unique (Regiospecifc) Cleavage of RNA by RNase H," FEBS Letters (1988) 226:232–234.

Hayase et al., "Secondary Structure in Formylmethionine tRNA Influences the Site–Directed Cleavage of Ribonuclease H Using ..." Biochemistry (1990) 29:8793–8797.

*Primary Examiner*—Gary L Kunz

(57) ABSTRACT

Oligonucleotides and other macromolecules are provided which have increased nuclease resistance, substituent groups for increasing binding affinity to complementary strand, and subsequences of 2'-deoxy-erythro-pentofuranosyl nucleotides that activate RNase H. Such oligonucleotides and macromolecules are useful for diagnostics and other research purposes, for modulating the expression of a protein in organisms, and for the diagnosis, detection and treatment of other conditions susceptible to oligonucleotide therapeutics.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-15 is confirmed.

* * * * *

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
      (A) LENGTH: 17 bases
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO:1:

CCACACCGAC GGCGCCC                                              17

(2) INFORMATION FOR SEQ ID NO:2:

(i) SEQUENCE CHARACTERISTICS:
      (A) LENGTH: 20 bases
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO:2:

CTTATATTCC GTCATCGCTC                                              20

(2) INFORMATION FOR SEQ ID NO:3:

(i) SEQUENCE CHARACTERISTICS:
       (A) LENGTH: 20 bases
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO:3:

TCCGTCATCG CTCCTCAGGG                                              20

(2) INFORMATION FOR SEQ ID NO:4:

(i) SEQUENCE CHARACTERISTICS:
       (A) LENGTH: 20 bases
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO:4:

AAAACGTCAG CCATGGTCCC                                              20

(2) INFORMATION FOR SEQ ID NO:5:

(i) SEQUENCE CHARACTERISTICS:
       (A) LENGTH: 18 bases
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO:5:

TTCTCGCTGG TGAGTTTC                                                18

(2) INFORMATION FOR SEQ ID NO:6:

(i) SEQUENCE CHARACTERISTICS:
       (A) LENGTH: 17 bases
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO:6:

TCTCGCTGGT GAGTTTC                                                 17

(2) INFORMATION FOR SEQ ID NO:7:

(i) SEQUENCE CHARACTERISTICS:
       (A) LENGTH: 20 bases
       (B) TYPE: nucleic acid
       (C) STRANDEDNESS: single
       (D) TOPOLOGY: linear (iv) ANTI-SENSE: yes (xi) SEQUENCE DESCRIPTION: SEQ ID NO:7:

TCCCGCCTGT GACATGCATT                                               20

(2) INFORMATION FOR SEQ ID NO:8:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:8:

TCCTCCTCCC CGCGGCGGGT                                               20

(2) INFORMATION FOR SEQ ID NO:9:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:9:

CTCGCCCGCT CCTCCTCCCC                                               20

(2) INFORMATION FOR SEQ ID NO:10:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:10:

TTCTCGCCCG CTCCTCCTCC                                               20

(2) INFORMATION FOR SEQ ID NO:11:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:11:

TTCTCCTCCT CCCCTGGCAG                                               20

(2) INFORMATION FOR SEQ ID NO:12:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:12:

CTGGCTTCTC CTCCTCCCCT                                               20

(2) INFORMATION FOR SEQ ID NO:13:

```
    (i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:13:
```

CCTGCTGGCT TCTCCTCCTC                                                     20

```
(2) INFORMATION FOR SEQ ID NO:14:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:14:
```

TCTGGCGCTG CACCACTCTC                                                     20

```
(2) INFORMATION FOR SEQ ID NO:15:

(i) SEQUENCE CHARACTERISTICS:
        (A) LENGTH: 47 bases
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:15:
```

ACATTATGCT AGCTTTTTGA GTAAACTTGT GGGGCAGGAG ACCCTGT                       47

```
(2) INFORMATION FOR SEQ ID NO:16:

(i) SEQUENCE CHARACTERISTICS:
        (A) LENGTH: 29 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:16:
```

GAGATCTGAA GCTTCTGGAT GGTCAGCGC                                           29

```
(2) INFORMATION FOR SEQ ID NO:17:

(i) SEQUENCE CHARACTERISTICS:
        (A) LENGTH: 35 bases
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:17:
```

GAGATCTGAA GCTTGAAGAC GCCAAAAACA TAAAG                                    35

```
(2) INFORMATION FOR SEQ ID NO:18:

(i) SEQUENCE CHARACTERISTICS:
        (A) LENGTH: 33 bases
        (B) TYPE: nucleic acid
        (C) STRANDEDNESS: single
        (D) TOPOLOGY: linear
```

(iv) ANTI-SENSE: yes (xi) SEQUENCE DESCRIPTION: SEQ ID NO:18:

ACGCATCTGG CGCGCCGATA CCGTCGACCT CGA                                                33

(2) INFORMATION FOR SEQ ID NO:19:

(i) SEQUENCE CHARACTERISTICS:
            (A) LENGTH: 20 bases
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO:19:

CGGGAGGCGG TCACATTCGG                                                               20

(2) INFORMATION FOR SEQ ID NO:20:

(i) SEQUENCE CHARACTERISTICS:
            (A) LENGTH: 20 bases
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO:20:

UAGGAGAUGC CUAAGGCUUU                                                               20

(2) INFORMATION FOR SEQ ID NO:21:

(i) SEQUENCE CHARACTERISTICS:
            (A) LENGTH: 20 bases
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO:21:

GCUAUGUCGA CACCCAAUUC                                                               20

(2) INFORMATION FOR SEQ ID NO:22:

(i) SEQUENCE CHARACTERISTICS:
            (A) LENGTH: 20 bases
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO:22:

CAUAGGAGAU GCCUAAGGCT                                                               20

(2) INFORMATION FOR SEQ ID NO:23:

(i) SEQUENCE CHARACTERISTICS:
            (A) LENGTH: 21 bases
            (B) TYPE: nucleic acid
            (C) STRANDEDNESS: single
            (D) TOPOLOGY: linear (iv) ANTI-SENSE: yes (xi) SEQUENCE DESCRIPTION: SEQ ID NO:23:

```
GCGUUTGCTC TTCTTCUUGC G                                               21
```

(2) INFORMATION FOR SEQ ID NO:24:

(i) SEQUENCE CHARACTERISTICS:
        (A) LENGTH: 21 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:24:

```
GCGUUUGCTC TTCTUCUUGC G                                               21
```

(2) INFORMATION FOR SEQ ID NO:25:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:25:

```
GTACCACAAG GCCTTTCGCG                                                 20
```

(2) INFORMATION FOR SEQ ID NO:26:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:26:

```
GTGCTCATGG TGCACGGTCT                                                 20
```

(2) INFORMATION FOR SEQ ID NO:27:

(i) SEQUENCE CHARACTERISTICS:
        (A) LENGTH: 20 bases
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:27:

```
UGCATCCCCC AGGCCACCAT                                                 20
```

(2) INFORMATION FOR SEQ ID NO:28:

(i) SEQUENCE CHARACTERISTICS:
        (A) LENGTH: 19 bases
        (B) TYPE: nucleic acid
        (C) STRANDEDNESS: single
        (D) TOPOLOGY: linear (xi) SEQUENCE DESCRIPTION: SEQ ID NO:28:

```
CGCAAAAAAA AAAAAACGC                                                  19
```